United States Patent
Chuang et al.

(10) Patent No.: US 10,494,466 B2
(45) Date of Patent: Dec. 3, 2019

(54) POLYMERS POLYMERIZED FROM AT LEAST FOUR MONOMERS, AND COMPOSITIONS AND USES THEREOF

(71) Applicant: ISP INVESTMENTS LLC, Wilmington, DE (US)

(72) Inventors: Jui-Chang Chuang, Wayne, NJ (US); Xuejun Liu, Whippany, NJ (US); Osama M. Musa, Bedminster, NJ (US); David C. Streuli, Wayne, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 14/763,590

(22) PCT Filed: Feb. 27, 2014

(86) PCT No.: PCT/US2014/018868
§ 371 (c)(1),
(2) Date: Jul. 27, 2015

(87) PCT Pub. No.: WO2014/149486
PCT Pub. Date: Sep. 25, 2014

(65) Prior Publication Data
US 2015/0353666 A1    Dec. 10, 2015

Related U.S. Application Data

(60) Provisional application No. 61/790,971, filed on Mar. 15, 2013.

(51) Int. Cl.
| | | |
|---|---|---|
| *C08F 226/10* | (2006.01) | |
| *A61K 8/04* | (2006.01) | |
| *A61K 8/81* | (2006.01) | |
| *A61Q 5/06* | (2006.01) | |
| *C08F 220/06* | (2006.01) | |
| *C08F 220/18* | (2006.01) | |
| *C08F 26/08* | (2006.01) | |

(52) U.S. Cl.
CPC ............ *C08F 226/10* (2013.01); *A61K 8/046* (2013.01); *A61K 8/8182* (2013.01); *A61Q 5/06* (2013.01); *C08F 26/08* (2013.01); *C08F 220/06* (2013.01); *C08F 220/18* (2013.01)

(58) Field of Classification Search
CPC .. A61K 8/046; A61K 8/8182; A61K 2800/10; A61Q 19/00; A61Q 17/04; A61Q 5/06; C08F 220/06; C08F 220/18; C08F 226/10; C08F 26/08
See application file for complete search history.

(56) References Cited

U.S. PATENT DOCUMENTS

| | | |
|---|---|---|
| 3,692,893 A | 9/1972 | Palmer |
| 5,997,855 A | 12/1999 | Liu |
| 2002/0076390 A1 | 6/2002 | Kanter et al. |
| 2004/0266953 A1 | 12/2004 | Charmot et al. |
| 2008/0207767 A1 | 8/2008 | Dobos et al. |
| 2011/0159300 A1 | 6/2011 | Rodowski et al. |
| 2012/0130036 A1 | 5/2012 | Ulmer et al. |

OTHER PUBLICATIONS

International Search Report, PCT/US2014/018868 published on Sep. 25, 2014.

*Primary Examiner* — Matthew P Coughlin
*Assistant Examiner* — Thurman Wheeler
(74) *Attorney, Agent, or Firm* — William J. Davis; Nathalie Tietcheu

(57) ABSTRACT

Family of non-homopolymers synthesized from N-vinyl lactam, (meth)acrylic acid, hydrophobic (meth)acrylic ester of a straightchain or branched-chain alkyl alcohol and monomer selected from the group consisting of functionalized and unfunctionalized: dialkyl maleates, dialkyl fumarates, and combinations thereof. The non-homopolymers may exhibit solubility in one or more lower molecular weight alcohols and/or a glass transition temperature greater than 80° C.

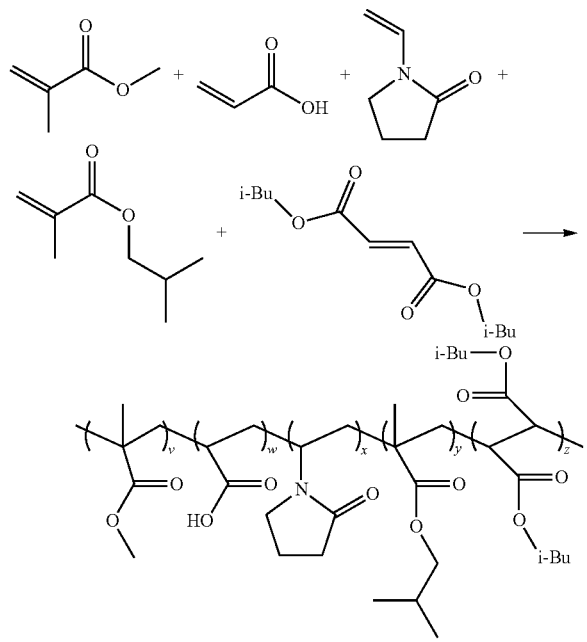

2 Claims, No Drawings

POLYMERS POLYMERIZED FROM AT LEAST FOUR MONOMERS, AND COMPOSITIONS AND USES THEREOF

The invention is directed to non-homopolymers that are synthesized from at least four polymerizable monomers, and may include one or more optional fifth monomer. In one embodiment, the polymers are soluble in at least one lower molecular weight alcohol such as methanol, ethanol, 1-propanol, or 2-propanol. Other aspects of the invention include non-homopolymers having a glass transition temperature greater than 40° C.

DESCRIPTION OF RELATED ART

Formulation scientists often face multiple challenges when developing new or reformulating existing products. Many times, products must attain target attributes that can only be achieved by one or more polymers, properties like UV absorption, adhesion, shine, smoothness, texture, binding, and/or water solubility/insolubility profile. For optimal performance, the polymer(s) should be soluble in an amenable solvent system, either during product formulation or end use. Due to its low toxicity, cost, and boiling point, ethanol and other low molecular weight alcohols may be a solvent of choice for many products, including cosmetics for use on the skin or hair.

Unfortunately, there is a limited selection of polymers soluble in lower molecular weight alcohols that also exhibit advanced functionality required for next-generation products. For example, while poly(vinyl alcohol) demonstrates excellent film strength, it flakes easily. To overcome these solubility and/or property deficiencies, polymers are often engineered as non-homopolymers to exploit the benefits of two or more monomer units. However, the polymer scientist must balance sometimes competing constraints between performance and solubility. Hence, needed are polymers that are soluble in the lower molecular weight alcohols which also satisfy the demands of product performance.

The related art teaches various polymers used in the cosmetic arts and their uses. Representative U.S. patent applications include 2002/0076390, 2002/0146515, 2004/0132863, 2005/0065252, 2005/0222322, 2005/0265949, 2007/0086959, 2010/0080763, and U.S. Pat. Nos. 4,486,577; 4,508,884; 5,662,892; 5,912,294; 6,126,929; 6,686,413; 7,048,916; 7,122,175; and 7,144,928. These publications teach polymers of differing compositions for use in applications ranging from cosmetics (e.g., hair, skin, nails) to floor polish and contact lens.

An acrylic resin is taught in U.S. patent application 2005/0065252 that is derived from a $C_1$ to $C_{14}$ (meth)acrylate, a 5- or more-member heterocyclic monomer, and a monomer having at least two olefinic double bonds. Composition [7] in this application is a polymer derived from a $C_1$ to $C_{14}$ (meth)acrylate, a 5- or more-member heterocyclic monomer, an alicyclic monomer, and a monomer containing at least one polar functional group such as a hydroxyl group. However, given the broad range in stated monomer levels, there is no indication that polymers of the '252 patent application should be ethanol soluble.

Personal care polymers are the subject of U.S. patent application 2002/0076390. The polymers are derived from 10%-85% (w/w) hydrophobic first monomer that is a (meth) acrylate of a $C_4$ to $C_{18}$ alkyl alcohol, 10%-70% (w/w) of a hydrophobic second monomer that is (meth)acrylate ester of a cyclic alcohol containing 6 to 20 carbon atoms, and up to 20% (w/w) of an optional hydrophilic third monomer, such as (meth)acrylamide, 2-ethoxyethyl (meth)acrylate or N-vinyl-2-pyrrolidone. The applications states, "The total amount of hydrophilic monomer preferably does not exceed about 20%, more preferably about 10% of the total weight of all monomers, such that excessive hydrophilicity is avoided." As a result of this composition, the application states the glass transition temperature ($T_g$) of the polymers is preferably less than 35° C. Example polymers in Table 1 of the '390 application have a $T_g$ of 15° C. or less, which means they exhibit rubber-like properties at room temperature, and may be too soft and/or tacky for many applications.

Also related is U.S. Pat. No. 7,122,175, which provides a reshapable hair styling composition comprising a (meth) acrylate ester of a $C_4$ to $C_{18}$ alkyl alcohol, a (meth)acrylate ester of a cyclic alcohol, at least one hydrophilic monomer, and, optionally, other monomer units. The '175 patent teaches broad ranges for the prescribed named monomer units. The synthesis methods disclosed in this patent include emulsion polymerization in water with dodecyl benzene sulfonate, solution polymerization in methylethyl ketone followed by inversion in water, and suspension polymerization in water. Additionally, the polymer of Example 1 is taught as a hair styling composition in water. However, the '175 patent does not disclose the existence of alcohol-soluble polymers, let alone enable one skilled in the art how to attain them. Furthermore, the polymers that are taught possess low glass transition temperatures, about −100° C. to about 15° C., which can render them sticky and tacky at room temperature, and which realistically limits their usefulness in the cosmetic arts like skin, sun, and hair care products.

Also related to application U.S. 61/750,582.

Despite the body of related work in polymer chemistry, there still exists a commercial and industrial need for polymers that are soluble in lower molecular weight alcohols, especially ethanol. Of particular value are alcohol-soluble polymers having a glass transition temperature greater than about 40° C. to enable their use in the cosmetic, adhesive, inks, and coatings arts.

SUMMARY

Polymers have been discovered that offer the scientist extended formulation and performance options in that the polymers may exhibit a solubility in lower molecular weight alcohols, and/or may have a glass transition temperature greater than 40° C. One or more of these properties may facilitate non-tacky and/or non-sticky polymers and compositions thereof. The polymers are synthesized from at least: (A) 9-32 mole percent of at least one N-vinyl lactam, (B) 24-30 mole percent of a (meth)acrylic acid, and combinations thereof, (C) 32-55 mole percent of at least one hydrophobic (meth)acrylic ester of a straight-chain or branched-chain alkyl alcohol, (D) 4-13 mole percent of a monomer selected from the group consisting of functionalized and unfunctionalized: dialkyl maleates, dialkyl fumarates, and combinations thereof, and optionally (E) up to 5 mole percent of one or more other monomers. In various embodiments the polymers may be used in personal care compositions such as sun-, skin-, and hair-care products, and in non-personal care formulas.

DETAILED DESCRIPTION

Described herein is a class of polymers synthesized from at least: (A) 9-32 mole percent of at least one N-vinyl lactam, (B) 24-30 mole percent of a (meth)acrylic acid, and combinations thereof, (C) 32-55 mole percent of at least one hydrophobic (meth)acrylic ester of a straight-chain or branched-chain alkyl alcohol, (D) 4-13 mole percent of a monomer selected from the group consisting of functionalized and unfunctionalized: dialkyl maleates, dialkyl fumarates, and combinations thereof, and optionally (E) up to 5 mole percent of one or more other monomers. The total monomer content in the polymers equals 100%. By selecting each monomer type and amount, polymers of the invention may be soluble in lower molecular weight alcohols, which may extend their use into the arts where alcohol-soluble polymers find application. For example, the polymers contain higher levels of hydrophilic monomers than taught in U.S. Pat. No. 7,122,175. In one embodiment the polymers may have a glass transition temperature greater than 40° C. In another embodiment, the polymers may be formulated in personal care products, such as for the sun care, skin care, or hair-care market segments.

As used herein, the following terms have the meanings set out below:

The term "halogen" refers to chloro, bromo, iodo and fluoro, and may be bromo or chloro. The term "halogenated" refers to compounds having one or more halogen substituents.

The term "heteroatom" refers to atoms such as oxygen, nitrogen, sulfur, and phosphorus.

The term "functionalized" refers to replacing one or more hydrogens with one or more non-hydrogen groups, for e.g., alkyl, alkoxy, cycloalkyl, alkenyl, cycloalkenyl, alkynyl, and/or aryl groups. Alkyl, alkenyl and/or alkynyl groups include $C_1$-$C_{60}$, more particularly $C_1$-$C_{36}$, and most particularly $C_1$-$C_{18}$ groups. Cycloalkyl groups include cyclopentane, cyclohexane, cycloheptane, and the like. Alkoxy groups include methoxy, ethoxy, n-propoxy, isopropoxy, and the like. Aryl groups include benzenes, naphthalenes (2 rings), anthracenes (3 rings), and the like.

The term "monomer" refers to a low molecular weight compound that can form covalent chemical bonds with itself and/or with other monomers, resulting in a polymer. Monomers represent repeating structural units of a polymer.

The term "polymer" refers to a compound synthesized from repeating structural units (monomers) that are connected by covalent chemical bonds. The definition includes oligomers. Polymers may be further functionalized (example by hydrolysis), crosslinked, grafted or end-capped. Non-limiting examples of polymers include homopolymers, non-homopolymers, copolymers, terpolymers, quaternary polymers, and homologues. A polymer may be a random, block, or an alternating polymer, or a polymer with a mixed random, block, and/or alternating structure. Polymers may further be associated with solvent adducts.

The term "non-homopolymer" refers to any polymer synthesized from more than one type of repeating structural units (monomers) connected by covalent chemical bonds. Examples of non-homopolymers include copolymers, terpolymers, tetramers and the like.

The term "copolymer" refers to a polymer synthesized from essentially of two types of repeating structural units (monomers). The definition includes copolymers having solvent adducts.

The term "terpolymer" refers to a polymer synthesized from essentially of three types of repeating structural units (monomers). The definition includes terpolymers having solvent adducts.

The term "tetramer" refers to a polymer synthesized from essentially of four types of repeating structural units (monomers). The definition includes tetramers having solvent adducts.

The term "(meth)acrylate" refers to acrylate and methacrylate. Similarly, the term "(meth)acrylamide" refers to acrylamide and methacrylamide. Similarly, (meth)acrylic acid refers to acrylic acid and methacrylic acid.

The term "solvent adduct" refers to a solvent molecule that is bonded to a compound, such as a polymer, by one or more covalent bonds, ionic bonds, hydrogen bonds, coordinate covalent bonds, and/or Van der Waals forces of attraction.

The term "lower molecular weight alcohol" refers to any alcohol having from one to 4 carbon atoms, and includes: methanol, ethanol, 1-propanol, 2-propanol, allyl alcohol, propargyl alcohol, 2-aminoethanol, ethylene glycol, methylpropargyl alcohol, 1-butyn-4-ol, 2-butyn-1-ol, 2-buten-1-ol, 2-butanol, 2-methyl-2-propanol, and t-butanol. In various aspects of the invention the lower molecular weight alcohol may be methanol, ethanol, 1-propanol, 2-propanol, and t-butanol.

The terms "ultraviolet" and "UV" mean electromagnetic radiation, especially solar electromagnetic radiation, with a wavelength from about 100 nm to about 400 nm, and includes the UV-A, UV-B, and UV-C subclassifications of such radiation.

The term "UV-A" means ultraviolet electromagnetic radiation with a wavelength from about 320 nm to about 400 nm, and includes UV-A1 (from about 340 nm to about 400 nm) and UV-A2 (from about 320 nm to about 340 nm).

The term "UV-B" means ultraviolet electromagnetic radiation with a wavelength from about 290 nm to about 320 nm.

The term "UV-C" means ultraviolet electromagnetic radiation with a wavelength from about 200 nm to about 290 nm.

The term "UV absorber" means any entity that absorbs, scatters, and/or reflects UV radiation.

The term "personal care composition" and cosmetics refer to such illustrative non-limiting compositions as skin, sun, oil, hair, and preservative compositions, including those to alter the color, condition, or appearance of the skin, hair, and nails. Potential personal care compositions include, but are not limited to, compositions for increased flexibility in styling, durable styling, increased humidity resistance for hair, skin, color cosmetics, water-proof/resistance, moisturizing, wear-resistance, and thermal protecting/enhancing compositions.

The term "performance chemicals composition" refers to any non-personal care composition. Performance chemicals compositions serve a broad spectrum of arts, and include non-limiting compositions such as: adhesives; agricultural, biocides, coatings, electronics, household-industrial-institutional (HI&I), inks, membranes, metal fluids, oilfield, paper, paints, plastics, printing, plasters, and wood-care compositions.

The term "oilfield formulation" refers to a composition that may be used in the exploration, extraction, recovery, or completion of any hydrocarbon-based fuel. Non-limiting examples of oilfield formulations include anti-agglomerants, emulsifiers, de-emulsifiers, gas hydrate inhibitors, kinetic hydrate inhibitors, shale swelling inhibitors, drilling fluids, drilling muds, friction reducers, rheology modifier, fracturing fluids, and/or scale inhibitors.

The term "coating formulation" refers to any composition suitable for application on a substrate in order to provide one or more desired functions, including, but not limited to protecting, smoothing, strengthening, decorating, color enhancing/altering, substrate preparing and/or texturizing. The substrate for a coating formulation may include, without limitation, paper, paper board, wood, inorganic substrate, woven and non-woven textiles, metal, leather, powder, plastic, polymer, glass, cement, ceramic, traffic, tile, rubber, sealant, cable, concrete, plasterboard, adhesives, fillers, primers, inks, fertilizers, pharmaceuticals, structural materials, molding, printing, inks, and the like. Examples of coating formulations include, without limitation, the following: paints, primers, stains, sealers, varnishes/polyurethanes, adhesives, waterproofers, wood hardeners. Coating formulations may be applied by brush, dauber, roll, strip/sheet, and/or trowel, or may be atomized and applied as a spray, mist, or droplet.

A "paint formulation" is a non-limiting, specific type of a "coating formulation". Paints may be water based or non-water based (i.e., solvent based). Paint formulations may be designed for any number of substrates, including wood, siding, dry wall, plaster, plastics, masonry, brick, tile, particle board, glass, stucco, concrete, and the like. Non-limiting examples of paints include exterior paints, interior paints, architectural paints, and automotive paints.

All percentages, ratio, and proportions used herein are based on a weight basis unless otherwise specified.

A first monomer involved in the polymerization is 9-32 mole percent of at least one N-vinyl lactam, such as N-vinyl-2-pyrrolidone or N-vinyl-2-caprolactam, or combinations thereof. The N-vinyl lactam may be functionalized or unfunctionalized, for example, with one or more alkyl groups. Suitable N-vinyl lactams include those represented by a structure

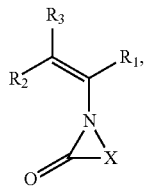

wherein X is a functionalized or unfunctionalized $C_1$-$C_5$ alkylene group optionally having one or more heteroatoms, and each $R_1$, $R_2$, and $R_3$ is independently selected from the group consisting of: hydrogen and functionalized and unfunctionalized alkyl groups optionally having one or more heteroatoms.

In particular embodiments, the first monomer (A) may be selected from the group consisting of:

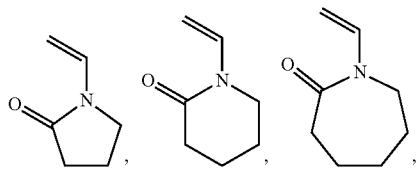

and combinations thereof. In other embodiments, a functionalized N-vinyl lactam may be used, including, but not limited to those represented by the structure:

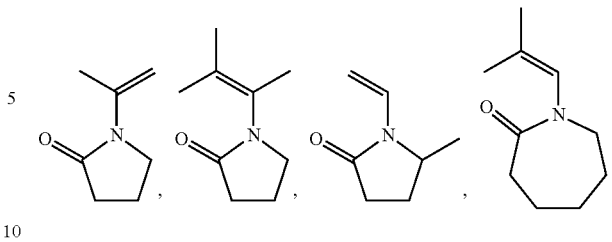

and combinations thereof and/or in combinations with other N-vinyl lactams presented earlier. One embodiment of the invention provides non-homopolymers having from about 24 to about 26 mole percent of monomer (A).

A second monomer used in the polymerizations to create the non-homopolymers is monomer (B), 24-30 mole percent of at least one (meth)acrylic acid. The (meth)acrylic acid may be functionalized or unfunctionalized acrylic acid, methacrylic acid, or their combinations. For example, the non-homopolymer may be synthesized using from about 24 to 26 mole percent of monomer (B).

The non-homopolymers also are synthesized from at least a third monomer (C), being 32-55 mole percent of at least one functionalized or unfunctionalized hydrophobic (meth)acrylic ester of a straight-chain or branched-chain alkyl alcohol. Monomers (C) may be represented by the structure:

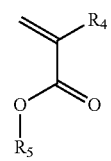

wherein $R_4$ is hydrogen or methyl or combinations thereof, and $R_5$ is a straight or branched alkyl group having from 1 to 50 carbon atoms that optionally may contain one or more heteroatoms. In various aspects, $R_5$ is a straight or branched alkyl group having from 1 to 18 carbon atoms. Particular (meth)acrylates of a straight or branched alkyl alcohol include methyl acrylate, methyl methacrylate (MMA), isobutyl acrylate (IBA), isobutyl methacrylate (IBMA), 2-ethylhexyl acrylate (EHA), 2-ethylhexyl methacrylate (EHMA), hydroxypropyl acrylate, tert-octyl acrylate, tert-octyl methacrylate, hydroxypropyl methacrylate (HPMA). In various embodiments monomer (C) may be MMA, IBMA, HPMA, or combinations thereof. In other embodiments monomer (C) may be a functionalized (meth)acrylate, such as an haloalkyl (meth)acrylate like trifluoroethyl (meth)acrylate or an alkylaminoalkyl (meth)acrylate such as t-butylaminoethyl (meth)acrylate. As a non-limiting illustration, the non-homopolymers may comprise from about 35 to 38 mole percent of one or more monomers (C).

A fourth monomer (D) is from about 4 to about 13 mole percent at least one functionalized or unfunctionalized dialkyl maleate or dialkyl fumarate. These compounds are recognized by one skilled in the art to be the cis and trans dialkyl ester isomers of butenedioic acid, and may be represented by the structures:

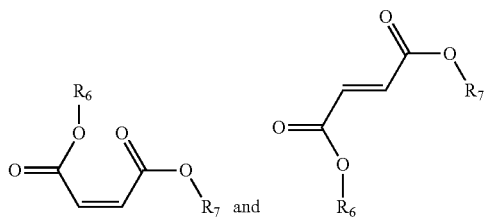

wherein each $R_6$ and $R_7$ is an independently selected straight or branched alkyl groups having from 1 to 50 carbon atoms that optionally may contain heteroatoms. In one embodiment, $R_6$ and $R_7$ are the same alkyl group. This monomer (D) may be selected from the group of functionalized and unfunctionalized dialkyl maleates and dialkyl fumarates wherein $R_6$ and $R_7$ are the same and have from 1 to 18 carbon atoms. Examples of the fourth monomer (D) include, without limitation, diisobutyl fumarate, dibutyl fumarate, diethyl maleate, dioctyl maleate, functionalized analogues thereof, and combinations thereof. In other embodiments, the non-homopolymer may be synthesized using from about 12 to about 13 mole percent of one or more dialkyl fumarate(s) and/or dialkyl maleate(s).

The non-homopolymers may include up to 5 mole percent of one or more optional monomer(s) (E), which may be functionalized or unfunctionalized, and may incorporated to further modulate the polymer solubilities (e.g., in ethanol, water, and/or a different solvent), and/or to impart polymer functionality for an intended application, such as glass transition temperature. In one embodiment, when the optional monomer(s) (E) are included, one or more may be PEG (meth)acrylate, PPG (meth)acrylate, or a functionalized analogue, such as a PEG (di)methacrylates or PEG tri(meth)acrylates or PEG/PPG (meth)acrylates. Functionalized (meth)acrylamides also may be used.

Further examples of the optional monomer (E) include functionalized and unfunctionalized 4-vinyl-1,2,3-triazoles, 5-vinyl-1,2,3-triazoles, (meth)acrylamides, (meth)acrylates, vinyls, allyls, maleic anhydrides, fumarates, maleates, maleimides, α,β-olefinically unsaturated carboxylic nitriles, styrenes, vinyl ethers, vinyl esters, vinyl acetates, vinyl amides, vinyl alcohols, vinyl carbonates, vinyl carbamates, vinyl thiocarbamates, vinyl ureas, vinyl halides, vinyl imidazoles, vinyl lactams, vinyl pyridines, vinyl silanes, vinyl siloxanes, vinyl sulfones, allyl ethers, and combinations thereof. In this aspect of the invention, the optional monomer may be selected from the group consisting of:

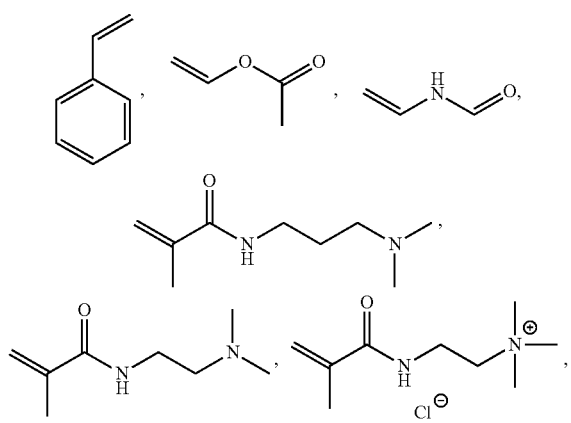

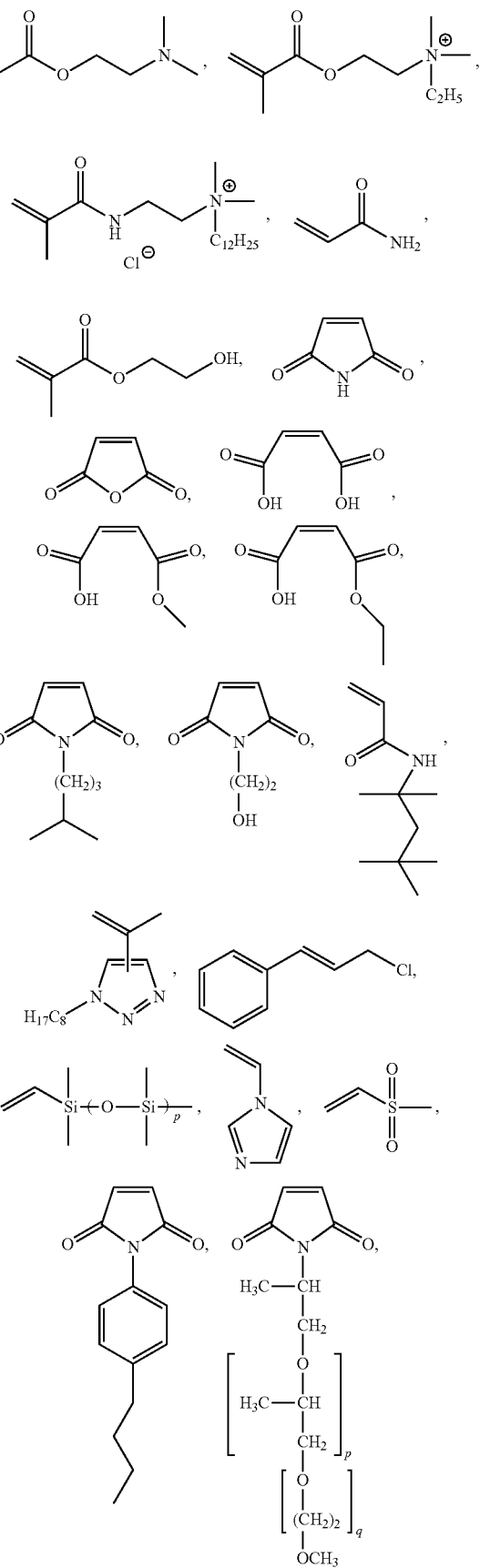

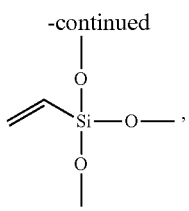

and combinations thereof, wherein each p and q are independently selected integers equal to or greater than 1. Of course, the non-homopolymer may comprise more than one monomer (E). Optional (E) monomers having one or more silane, siloxane, or quaternary amine groups may be suitable when the non-homopolymer finds application in skin and/or hair products.

The polymers embraced by the present invention may demonstrate solubility in lower molecular weight alcohols, for example, the polymers may exhibit ethanol solubility. In a first embodiment, the polymer may be at least 5% (w/w) soluble in at least one lower molecular weight alcohol, more particularly may be at least 40% (w/w) soluble, in at least one lower molecular weight alcohol, and yet more particularly may be at least 50% (w/w) soluble, in at least one lower molecular weight alcohol. In various other embodiments the lower molecular weight alcohol may be ethanol, 1-propanol, 2-propanol, or t-butanol. The Examples illustrate polymer synthesis at 50% (w/w) solids in a lower molecular weight alcohol, although the polymers also may be infinitely soluble and only limited by the viscosity attained.

The inventors have discovered that as a result of the types and amounts of monomer units, polymers of the invention may display a glass transition temperature higher than known in the related art. Whereas polymers of U.S. patent application 2002/0076390 and U.S. Pat. No. 7,122,175 are characterized by low glass transition temperatures from about −100° C. to about 15° C., polymers of the invention may not exhibit rubber-like behavior at room temperature. In various embodiments, the polymers may have a glass transition temperature greater than 40° C., more particularly greater than 80° C., and yet more particularly greater than 100° C. As the polymers may not be tacky at room temperature, they may find application in a number of uses where a non-tacky, non-sticky polymer is needed. This property may be enhanced by the polymers' solubilities in lower-molecular weight alcohols, e.g., to assist dissolving, dispersing, formulation, carrying, or delivering the polymer(s).

Many different polymers may be synthesized using the methods described above. By way of illustration, the invention includes the following, non-limiting examples:
poly(VP-AA-MMA-IBMA-DIBF),
poly(VP-AA-MMA-IBMA-DIBF-tBAEMA),
poly(VP-AA-MMA-IBMA-DIBF-TFEMA),
poly(VP-AA-MMA-IBMA-DIBF-PEG/PPGMA),
poly(VP-AA-MMA-IBMA-DBM),
poly(VP-AA-MMA-IBMA-DBM-tBAEMA),
poly(VP-AA-MMA-HPMA-DOM-tBAEMA),
poly(VP-MAA-MMA-HPMA-DOM-tBAEMA),
poly(VP-AA-MMA-HPMA-DEM-tBAEMA),
poly(VP-AA-MMA-HPMA-DIBF-tBAEMA),
poly(VP-MAA-IBMA-HPMA-DIBF-tBAEMA),
poly(VP-MAA-IBMA-HPMA-DIBF-tBAEMA),
where the following abbreviations are employed: VP (N-vinyl-2-pyrrolidone), AA (acrylic acid), MAA (methacrylic acid), MMA (methyl methacrylate), IBMA (iso-butyl methacrylate), DIBF (di-iso-butyl fumarate), tBAEMA (tert-butylaminoethyl methacrylate), TFEMA (trifluoroethyl methacrylate), PEG/PPGMA (polyethylene glycol/polypropylene glycol methacrylate), DBM (dibutyl maleate), DOM (dioctyl maleate), DEM (diethyl maleate), and HPMA (hydroxypropyl methacrylate).

In addition to these polymers, others are embraced by the invention. For example, VCL (N-vinyl-2-caprolactam) may replace part or all of the VP in these polymers. It may be necessary to adjust the type and amount of hydrophobic monomers or add/introduce hydrophilic monomers in order to maintain a solubility in lower molecular weight alcohols. Other dialkyl maleates that may be used in part or to replace those presented earlier include: dimethyl maleate, dipropyl maleate, di-n-butyl maleate, di-sec-butyl maleate, and diethylhexyl maleate. The corresponding dialkyl fumarates also may be used.

Radical polymerization methods known to one skilled in the art may be employed to create the polymers described herein. These methods include, but are not limited to: solution polymerization, emulsion polymerization, and precipitation polymerization. Free radical polymerization may be employed when using thermally decomposed polymerization initiators, and is described in "Decomposition Rate of Organic Free Radical Polymerization" by K. W. Dixon (section II in *Polymer Handbook, volume 1, 4$^{th}$ edition*, Wiley-Interscience, 1999), which is incorporated by reference. Another description of the free-radical polymerization process is given in U.S. Pat. No. 2,882,262.

The reactants, comprising the at least four polymerizable monomers, may be charged in portions or charged together into a reactor and stirred at a temperature to facilitate the reaction, being limited only by the decomposition temperature of any reactant. The reaction can be performed with and without added solvent. The addition of an optional inert solvent may be beneficial when a high viscosity of the reacting system limits effective reactive processing (i.e., has a high viscosity).

It is within the scope of this invention to employ any combination of the described polymerizable unit(s) [e.g., N-vinyl lactams, (meth)acrylic acids, (meth)acrylates]. It may be advantageous to add the least reactive reactants first, and the more reactive ones later in the preparation. As necessary, additional reactive species can be attached to the polymer.

It may be beneficial and desirable to remove any amount of unreacted reactant and/or side product from the final reaction product using methods that are known in the art, including distillation, inversion precipitation, and chromatography.

The reaction may be carried out for times ranging from 30 seconds to 48 hours or even more, and may depend upon factors that include (1) the reactivity of the reactants, (2) the number of reactive groups, since one or more of the reactants may have more than one reactive group, (3) steric hindrance surrounding any reactive site, (4) the reaction temperature employed, (5) the presence or absence of a solvent, and (6) the use or non-use of an initiator and/or catalyst. With the use of an optional reaction solvent or solvents, it may be particular to remove the solvent(s) after the reaction, e.g., at reduced pressure and/or elevated temperature, and then to add a different solvent conducive to the final formulation.

Typically, the molecular weight of the polymer ranges from about 1,000 Da to about 5,000,000 Da, and more particularly the molecular weight ranges from about 10,000 Da to about 1,000,000 Da. As described later, the molecular weight of a synthesized product may be altered by the addition of an optional chain transfer agent (such as isopropanol or carbon tetrabromide) in the customary amounts to the reaction vessel.

For solution reactions, temperatures may be conveniently controlled by judicious choice of solvents within an appropriate boiling range. Temperatures in this case range from 40° C. to about 140° C., particularly from 50° C. to 120° C., and more particularly from 60° C. to 100° C. Reaction times for solution reaction range from several minutes to 48 hours or more. Higher reaction temperatures and highly reactive reactants will reduce time for conversion to the desired product(s). Reaction times may range between 60 minutes and 12 hours, and more particularly between 120 minutes and 10 hours.

Due to the broad nature of the invention, in general a free radical addition polymerization initiator may be beneficial. However, in some synthesis routes, an initiator is not needed to produce the disclosed polymers.

Free-Radical Polymerization

Compounds capable of initiating the free-radical polymerization include those materials known to function in the prescribed manner, and include the peroxide and azo classes of materials. Exemplary peroxide and azo compounds include, but are not limited to: acetyl peroxide; azobis-(2-amidinopropane) dihydrochloride; azobis-isobutyronitrile (AIBN); 2,2'-azobis-(2-methylbutyronitrile); benzoyl peroxide; di-tert-amyl peroxide; di-tert-butyl diperphthalate; tert-butyl peroxy-2-ethylhexanoate; tert-amyl peroxy-2-ethylhexanoate; tert-butyl hydroperoxide; tert-butyl peroxybenzoate; tert-butyl peroxymaleate; tert-butyl peroxyisobutylrate; tert-butyl peroxyacetate; tert-butyl peroxypivalate; para-chlorobenzoyl peroxide; cumene hydroperoxide; diacetyl peroxide; dicumyl peroxide; didecanoyl peroxide; dilauroyl peroxide; diisopropyl peroxodicarbanate; dioctanoyl peroxide; succinyl peroxide; and bis-(orthotoluoyl) peroxide. Tert-amyl peroxy-2-ethylhexanoate is a particular initiator for a number of the particular compositions described herein.

Also suitable to initiate the free-radical polymerization are initiator mixtures or redox initiator systems, including: ascorbic acid/iron(II) sulfate/sodium peroxodisulfate, tert-butyl hydroperoxide/sodium disulfite, and tert-butyl hydroperoxide/sodium hydroxymethanesulfinate.

A chain transfer agent optionally may be used to control the degree of polymerization of the polymer, and thereby control the molecular weight and molecular weight distribution of the product. As a skilled artisan can appreciate, the chain transfer agent may become part of the polymer.

The chain transfer agent may be of the kind that has a carbon-sulfur covalent bond. The carbon-sulfur covalent bond has usually absorption peak in a wave number region ranging from 500 to 800 cm$^{-1}$ in an infrared absorption spectrum. When the chain transfer agent is incorporated into the polymer, the absorption peak of the product may be changed in comparison to product made without a chain transfer agent.

Exemplary chain transfer agents include, but are not limited to, n-$C_3$-$C_{15}$ alkylmercaptans such as n-propylmercaptan, n-butylmercaptan, n-amylmercaptan, n-hexylmercaptan, n-heptylmercaptan, n-octylmercaptan, n-nonylmercaptan, n-decylmercaptan, and n-dodecylmercaptan; branched alkylmercaptans such as isopropylmercaptan, isobutylmercaptan, s-butylmercaptan, tert-butylmercaptan, cyclohexylmercaptan, tert-hexadecylmercaptan, tert-laurylmercaptan, tert-nonylmercaptan, tert-octylmercaptan, and tert-tetradecylmercaptan, allylmercaptan; aromatic ring-containing mercaptans such as, 3-phenylpropylmercaptan, phenylmercaptan, and mercaptotriphenylmethane. As a skilled artisan understands, the term -mercaptan and -thiol may be used interchangeably to mean C—SH group.

Typical examples of such chain transfer agents also include, but are not limited to, dodecanethiol, butanethiol, isooctyl-3-mercaptopropionate, 2-methyl-5-tert-butyl-thiophenol, carbon tetrachloride, carbon tetrabromide, and the like. Dodecanethiol and carbon tetrabromide are most typically used.

Based on total weight of the monomers to be synthesized, the chain transfer agent may generally be present in an amount from about 0.1% to about 7%, including from about 0.5% to about 6%, and from about 1.0% to about 5%, although it may be present in greater or lesser amounts.

The alcohol-soluble polymers described herein may be used in a variety of compositions that can be broadly categorized as personal care compositions or cosmetic compositions (meaning for use on or in the body of a mammal, especially man) and performance chemicals compositions (meaning they are not personal care compositions). The compositions may contain a lower molecular weight alcohol as part of the formulation (since it will dissolve or help to dissolve the polymer in the composition), and/or may be those compositions that come into contact with an alcohol during use (e.g., films created upon the alcohol wetting of polymer powders). The compositions, however, are not required to comprise an alcohol, but instead by comprise other materials, e.g., liquids, gels, and/or semi-solids, to assist in the delivery and/or performance of the invention's polymers.

Personal Care Compositions

The, homopolymers and/or non-homopolymers described herein may be used alone or in combination with other ingredient(s) in various compositions and product forms. Such compositions include, but are not limited to personal care compositions, adhesives, coatings, paints, electronics, Household, Industrial and Institutional (HI&I) compositions, inks, membranes, metal working fluids, oilfield chemicals, plastics and plasticizers, textiles, industrial products, biocides, pharmaceuticals/nutritionals, and agrochemical compositions.

The term "personal care composition" refers to a composition intended for use on or in the human body. Non-limiting, but specific types of personal care compositions include hair care compositions (encompassing styling and non-styling compositions), sun care compositions (encompassing after-sun compositions), skin care compositions, and oral care compositions.

Non-limiting applications of the hair care compositions include: hair styling, hair setting, hair sculpting, hair curling, hair holding, hair waving, hair fixing, hair maintaining, hair shaping, hair straightening, hair volumizing, hair relaxing, shampooing, hair conditioning, hair cleansing, promoting hair style durability, imparting humidity resistance to hair and hair styles, enhancing hair shine, repairing split ends of hair, enhancing hair manageability such as lightness, smoothness, softness, disentangling and/or suppleness of hair, modulating hair stylability, protecting hair from thermal damage, hair dyeing, hair coloring, hair bleaching, oxidation dyeing of hair, limiting hair color bleeding, protecting hair color, hair treating (e.g., anti-dandruff), anti-hair fall, and protecting hair from UV radiation.

The hair care compositions of the invention may be particularly used in hair styling. More particularly, the hair care compositions may be used to improve the hair stiffness, curl retention, and/or hair conditioning.

In particular embodiments, the hair care compositions may comprise the polymer(s) described herein in an amount from about 0.1% to about 50% by weight of the composition. More particularly, the polymer(s) may be present in an amount from about 0.5% to about 20% by weight, most particularly from about 1% to about 10% by weight of the composition.

The hair care compositions may further comprise one or more additional ingredients. Particularly, the additional ingredients may be selected from the group consisting of: skin care or hair care agents, hair styling agents, hair fixative agents, film formers, structurants, gelling agents, surfactants, thickeners, preservatives, viscosity modifiers, electrolytes, pH adjusting agents, perfumes, dyes, organosilicon compounds, anti-dandruff agents, anti-foaming agents, anti-frizz agents, penetrants, vitamins, conditioning agents, chelating agents, antimicrobial agents, preservatives, UV absorbers, sunscreens, natural extracts, propellants, carriers, diluents, solvents, pharmaceutical actives, lubricants, combing aids, plasticizers, solubilizers, neutralizing agents, vapor pressure suppressants, bleaching agents, hydrating agents, moisturizers, cosmetic adjuvants and/or additives, protectants, and mixtures thereof.

Non-limiting applications of the sun care compositions include: protecting skin and/or hair from UV radiation (including any or all of UV-A, UV-B and/or UV-C radiation), sun screening, skin anti-irritating, skin repairing, skin wrinkle masking, skin nourishing, skin moisturizing, skin relaxing, skin refreshing, skin cooling, skin soothing, skin tanning, skin tan prolonging, sun-less skin tanning, skin glowing, skin micro-glittering, skin shimmering, and skin anti-tanning.

Non-limiting applications of the skin care compositions include: protecting skin from UV radiation (including any or all of UV-A, UV-B and/or UV-C radiation), skin cleansing, face cleansing, body cleansing, insect repelling, antiperspirant, exfoliating skin, rejuvenating skin, influencing cell turnover, deodorant, astringent, imparting water resistance or water proofness to skin, decreasing and/or minimizing the appearance of skin wrinkles, decreasing and/or minimizing the appearance of skin blemishes (such as lentigo, skin discolorations, pimples, and/or acne), changing skin color (including skin lightening, skin brightening, skin color darkening, and color cosmetics for the face, cheeks, lips, eyelids, and/or eye lashes), skin iridescing, skin glossing, curling of eye lashes, eye lining, eye shadowing, mascara, removing facial and/or body hair, skin tightening, skin tanning, skin bronzing, skin blushing, prolonging skin tan, sun-less skin tanning, anti-tanning, skin antibacterial, skin anti-oxidant, skin anti-photoaging, skin anti-seborrheic, cell exchange and/or cell respiration activating of skin, skin conditioning, skin detoxifying, skin emollient, skin moisturizing, film forming on skin, skin healing-cicatrizing, skin immune-protecting, skin plumping, glossing, shading, plumping, and/or coloring of lips, skin revitalizing, skin energizing, skin re-sculpting, skin nourishing, skin smoothing, skin slimming, skin anti-irritating, and skin sanitizing.

Non-limiting applications of the oral care compositions include: tooth and/or mouth cleansing, providing denture adhesion, delivering and/or retaining actives to oral cavity, mouth washing, mouth refreshing, mouth rinsing, mouth gargling, providing oral hygiene, preventing, reducing, controlling, and/or removing tooth stain, preventing and/or controlling tooth decay, preventing and/or controlling tartar, tooth flossing, tooth whitening and/or bleaching, mouth treating, and tooth filling.

The polymers described herein also may be used alone or in combination with other ingredient(s) in pharmaceutical and/or nutritional compositions.

Non-limiting applications of the pharmaceutical and/or nutritional compositions include: providing anti-tack, binder, coating, disintegrating, dispersing, encapsulating, filling, film forming, lubricating, and solubilizing. Additional insight into how the polymers described herein find application in this art area may be found in the following publications by Ashland Specialty Ingredients: *Health and nutrition product guide—Performance enhancing products* (08/2008), *Plasdone™ povidones product overview* (04/2010), *Plasdone™ K-12 and K-17 povidones—Solubilizers for liquid softgel fill formulations* (09/2010), *Plasdone™ K-29/32 povidone—High efficiency binder for wet granulation* (04/2010), *Plasdone™ S-630 copovidone—Product Overview* (04/2010), *Polyplasdone™ Ultra and Ultra-10 crospovidones—Product overview* (09/2010), *Polyplasdone™ superdisintegrants—Product overview* (07/2010), *Polyplasdone™ crospovidone—Superdisintegrants for orally disintegrating and chewable tablets* (07/2010), *Polyplasdone™ crospovidone—Nonionic superdisintegrant for improved dissolution of cationic drugs* (07/2009), *Polyplasdone™ crospovidone—The solution for poorly soluble drugs* (07/2009), *Polyplasdone™ crospovidone—Novel pelletization aid for extrusion spheronization* (07/2010), *PVP-Iodine povidone iodine antiseptic agent* (03/2004), and *Pharmaceutical technical bulletin—PVP-Iodine for prophylaxis and treatment of bovine mastitis* (12/2003). Each publication is hereby incorporated in its entirety by reference.

Any range in composition pH may be used. In embodiments wherein the composition is applied to keratinous material, the pH may range from about 2 to 12. pH may be adjusted to a desired value by means of adding one or more acidifying or alkalinizing agents that are well-known in the state of the art. For example, the composition can contain at least one alkalizing or acidifying agent in amounts from about 0.01% to about 30% based on the total weight of the composition.

Non-limiting examples of acidifying or acidic pH adjusting agents include organic acids, such as citric acid, acetic acid, carboxylic acids, $\alpha$-hydroxyacids, $\beta$-hydroxyacids, $\alpha,\beta$-hydroxyacids, co-hydroxyacids, salicylic acid, tartaric acid, lactic acid, glycolic acid, natural fruit acids, and combinations thereof. In addition, inorganic acids, for example hydrochloric acid, nitric acid, sulfuric acid, sulfamic acid, phosphoric acid, and combinations thereof can be utilized.

Non-limiting examples of alkalizing or alkaline pH adjusting agents include ammonia, alkali metal hydroxides (such as sodium hydroxide and potassium hydroxide), ammonium hydroxide, alkanolamines (such as mono-, di- and triethanolamine), diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis (hydroxypropyl)ethylenediamine, hydroxyalkylamines and ethoxylated and/or propoxylated ethylenediamines, alkali metal salts of inorganic acids, such as sodium borate (borax), sodium phosphate, sodium pyrophosphate, and the like, and mixtures thereof.

Non-limiting examples of alkalizing agent can be chosen from ammonia, alkali carbonates, alkanolamines, like mono-, di- and triethanolamines, as well as their derivatives, sodium or potassium hydroxides and compounds of the following formula:

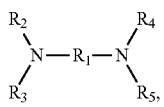

wherein $R_1$ is a propylene residue that may be optionally substituted with an hydroxyl group or a C1-C4 alkyl radical; $R_2$, $R_3$, $R_4$ and $R_5$ are identical or different and represent a hydrogen atom, a C1-C4 alkyl radical or C1-C4 hydroxyalkyl radical.

The composition also may comprise one or more buffers. Suitable buffering agents include but are not limited to alkali or alkali earth carbonates, phosphates, bicarbonates, citrates, borates, acetates, acid anhydrides, succinates and the like, such as sodium phosphate, citrate, borate, acetate, bicarbonate, and carbonate. The personal care compositions may be formulated in any of the product forms known to a person of ordinary skill in the art. Non-limiting product forms are described below.

Product Forms

Non-limiting hair care product forms include: shampoos, conditioners, aerosols, mousses, sprays, mists, gels, waxes, creams, lotions, glues, pomades, spritzes, solutions, oils, liquids, solids, W/O emulsions, 0/W emulsions, suspensions, multiple emulsions, microemulsions, microencapsulated products, sticks, balms, tonics, pastes, reconstitutable products, nanoemulsions, solid lipid nanoparticles, liposomes, cubosomes, neosomes, putties, lacquers, serums, perms, volumizers, packs, flakes, 2-in-1 shampoo/conditioner products, and 3-in-1 shampoo/conditioner/styling products.

The compositions according to the invention may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process.

Non-limiting sun care product forms include: solutions, liquids, creams, powders, lotions, gels, pastes, waxes, aerosols, sprays, mists, roll-ons, sticks, milks, emulsions, and wipes.

Non-limiting skin care product forms include: solutions, oils, lotions, creams, ointments, liquids, gels, solids, W/O emulsions, 0/W emulsions, milks, suspensions, microemulsions, dispersions, microencapsulated products, sticks, balms, tonics, pastes, mists, reconstitutable products, peels, soaps, aerosols, mousses, waxes, glues, pomades, spritzes, putties, lacquers, serums, perms, powders, pencils, flakes, blush, highlighters, bronzers, concealers, and 2-way cake products.

The compositions of the invention may also take the form of skin-washing compositions, and particularly in the form of solutions or gels for the bath or shower, or of make-up removal products.

The six skin care product categories that follow next may be considered a subset of the skin and sun care products:

(1) Eye Care

Non-limiting eye care product forms include: mascaras, eye liners, eye shadows, curlers of eye lashes, eyebrow pencils, and eye pencils.

(2) Lip Care

Non-limiting lip care product forms include: lipsticks, lip balms, lip pencils, lip glosses, lip sprays, transparent lip bases, tinted lip moisturizers, and multi-functional color sticks that can also be used for cheeks and eyes.

(3) Nail Care

Non-limiting nail care product forms include: nail polishes, nail varnishes, enamels, nail varnish removers, home-manicure products such as cuticle softeners and nail strengtheners, and artificial nails.

(4) Face Care

Non-limiting face care product forms include: creams, lotions, solutions, oils, liquids, peels, scrubs, emulsions, suspensions, microemulsions, microencapsulated product, pastes, reconstitutable product, aerosols, mousses, gels, waxes, glues, pomades, spritzes, facial wet-wipes, putties, lacquers, serums, perms, powders, blush, highlighters, bronzers, masks, and concealers.

(5) Body Care

Non-limiting body care product forms include: foams, peels, masks, gels, sticks, aerosols, lotions, salts, oils, balls, liquids, powders, peels, pearls, bar soaps, liquid soaps, body washes, cleansers, scrubs, creams, flakes, other bath and shower products, shaving products, waxing products, and sanitizers.

(6) Foot Care

Non-limiting foot care product forms include: mousses, creams, lotions, powders, liquids, sprays, aerosols, gels, flakes, and scrubs.

Non-limiting oral care product forms include: toothpastes, adhesives, gums, gels, powders, creams, solutions, lotions, liquids, dispersions, suspensions, emulsions, tablets, capsules, rinses, flosses, aerosols, strips, films, pads, bandages, microencapsulated products, syrups, and lozenges.

Also contemplated are personal care compositions comprising polymer(s) described herein complexed with iodine. These compositions may be used in treating skin conditions, non-limiting examples of which include dermatitis, wounds, bacterial infections, burns, rashes, and herpes. These complexed compositions may be staining, substantially non-staining, or essentially non-staining.

Examples of related personal care compositions are disclosed in U.S. Pat. Nos. 5,599,800; 5,650,166; 5,916,549; and 6,812,192; U.S. patent application 2009/0317432; EP 556,660; 661,037; 661,038; 662,315; 676,194; 796,077; 970,682; 976383; 1,415,654; and 2,067,467; and WO 2005/032506; each of which is hereby incorporated in its entirety by reference.

It is also contemplated that the personal care compositions may be used in products for male and/or female personal grooming and/or toiletry such as: sanitary napkins, baby diapers, adult diapers, feminine products, products for incontinence, and other related products.

An array of additional personal care compositions, methods, and uses are contemplated. Disclosure of these compositions may be found in the following brochures by Ashland Specialty Ingredients, each of which is hereby incorporated in its entirety by reference: *Plasdone™ K-29/32, Advanced non-oxidative, non-abrasive teeth whitening in toothpastes, mouthwashes, and oral rinses* (2010), *Polymers for oral care, product and applications guide* (2002), *A formulation guide for excellent hair styling gels and lotions* (4/2003), *PVP (polyvinylpyrrolidone)* (no date provided), and *Textile chemicals, solutions for the most challenging product environment* (no date provided).

Also contemplated are additional personal care compositions that may comprise the polymers described herein. Disclosures on such compositions may be found in the publications listed below, each of which is hereby incorporated in its entirety by reference: (1) Prototype Formulations—Personal Care Products (2009) from Xiameter, Dow Corning. (2) Sun care formulations under the category "Refreshing Sun", "Younger Sun", "Sun for Men", and "Sunny Glow" from Dow Corning. (3) Cosmetic Nanotechnology, Polymers and Colloids in Cosmetics, 2007, ACS Symposium Series. (4) Review Paper: Lipid nanoparticles (SLN, NLC) in cosmetic and pharmaceutical dermal products, International Journal of Pharmaceutics, Volume 366, 2009.

Optional: Additional Composition Ingredients

It is also contemplated that the personal care compositions optionally may contain one or more additional ingredients.

Further, it is contemplated that the composition ingredients may be formulated in a single container, or the ingredients may be formulated in-part in two or more distinct containers of the same or different type, the contents of which may require mixing prior to use.

Furthermore, it also is contemplated that the compositions may be prepared in the form of concentrates that may be diluted by a suitable substance(s) prior to use. The concentrate may, in turn, be present in any of the forms as described under 'Product Forms' for the personal care compositions of the invention.

A non-limiting list of classes of additional ingredients that may optionally be present in different types of personal care compositions is provided below: conditioning agents, antimicrobials, protectives (for example, antiradical agents), abrasives, UV absorbers, emulsifiers (including, but not limited to ethoxylated fatty acids, ethoxylated glyceryl esters, ethoxylated oils, ethoxylated sorbitan esters, fatty esters, PEG esters, polyglycerol esters), antiperspirants (including, but not limited to aluminium chlorohydrates, aluminium zirconium chlorohydrates), antioxidants, vitamins and/or provitamins, botanicals, fixatives, oxidizing agents, reducing agents, dyes, cleansing agents, anionic, cationic, nonionic, and/or amphoteric surfactants, thickeners and/or gelling agents, perfumes, flavors, and/or fragrances, pearlizing agents, stabilizers, pH adjusters, filters, antimicrobial agents, preservatives and/or disinfectants, associative polymers, oils of vegetable, mineral, and/or synthetic origin, polyols, silicones, colorants, bleaching agents, highlighting agents, propellants (including, but not limited to hydrocarbons, dimethyl ether, fluorocarbons), styling polymers, benefit agents, skin lighteners (including, but not limited to arbutin and kojic acids), tanning agents (including, but not limited to dihydroxyacetone), solvents and/or cosolvents, diluents, essential oils, sequestrants and/or chelators, carriers, and natural extracts and/or natural products.

The amount of each ingredient in the composition varies depending on the type of composition, the function and/or physicochemical property of the ingredient, and the amount of other co-ingredients. The precise amount of each ingredient may be easily determined by any person skilled in the related arts.

It may be desirable to include one or more ingredients described in the prior art disclosures IPCOM000186541D, IPCOM000128968D, and IPCOM000109682D on www.ip.com, the contents of each of these disclosures are hereby incorporated in their entirety by reference.

Further reference to formulary co-ingredients and product forms include the disclosures in US 2010/0183532, paragraphs [0096]-[0162], and WO 2010/105050, paragraphs [0053]-[0069], the contents of which are hereby incorporated in their entirety by reference.

Non-limiting examples of structurants that may be used in the hair care compositions according to the invention include dextrin palmitate, trihydroxystearin, hydroxy stearic acid, hydrophilic or hydrophobic silica, hydrophobically modified clay selected from the group consisting of: stearalkonium hectorite, quaternium-18 bentonite, quaternium-18 hectorite, disteardimonium hectorite, derivatives thereof, and mixtures thereof.

The hair care compositions of the invention may additionally comprise one or more hair styling agents, hair fixative agents, and/or film formers.

Particularly useful as styling agents are hair styling polymers. The hair styling polymers may be cationic, anionic, amphoteric or nonionic in nature. The polymers may be synthetic or naturally derived. Non-limiting examples of hair styling polymers include the following polymer products available for sale from Ashland Specialty Ingredients: (1) Cationic styling polymers with hair conditioning benefits—Styleze™ W Polymer, Styleze™ CC-10 (pseudo cationic), Gafquat™ 755 NP, and Gafquat™ 440; (2) Styling polymers with excellent high humidity curl retention—Styleze™ 2000, Allianz™ LT 120, Styleze™ W Polymer, and Advantage™ LCA; (3) Non-ionic styling polymers with broad ingredient compatibility—Polyvinylpyrrolidones such as PVP K-30, PVP K-60 and PVP K-90, Vinylpyrrolidone/vinyl acetate copolymers such as PVP/VA (E, I or W) 735, PVP/VA (E or W) 635, PVP/VA (E or I) 535, PVP/VA (E or I) 335 and PVP/VA S-630, and poly(vinylpyrrolidone/dimethylaminoethylmethacrylate) polymers such as Copolymer 845/937. Additional details on the aforementioned polymers and methods of use, or formulations thereof, may be found in a publication from Ashland Specialty Ingredients titled "*A Formulation Guide for Excellent Hair Styling Gels and Lotions*" (2002) that is hereby incorporated in its entirety by reference.

A non-limiting example of hair fixative agent that may be used in hair care compositions according to the invention includes a hair fixative polymer available for sale from Ashland Specialty Ingredients, AquaStyle™ 300 (INCI name Polyquaternium-69). A related publication from Ashland Specialty Ingredients titled "*Aquastyle™ 300, A Fixative Polymer with Enhanced Styling Benefits*" (2007) is hereby incorporated in its entirety by reference.

Non-limiting examples of film formers that may be used in hair care compositions according to the invention include film forming polymers available for sale from Ashland Specialty Ingredients such as (1) Aquaflex™ FX 64, (2) AquaCat™ clear cationic solution, (3) Aqualon™ carboxymethylcellulose, (4) Klucel™ hydroxypropylcellulose, and (5) Primaflo™ HP22 polymer solution.

Further details on hair styling agents, hair fixative agents, and/or film formers may be found in U.S. Pat. Nos. 7,871,600, 7,205,271, 7,122,175, 7,041,281, 6,998,114, 6,749,836, 6,689,346, 6,599,999, 6,562,325, 6,413,505, 6,387,351, 6,228,352, 5,643,581, 5,922,312, 5,897,870, 5,879,669, 5,709,850, 5,753,216 and 5,632,977 each of which is hereby incorporated in its entirety by reference.

Non-limiting examples of anti-frizz agents that may be used in hair care compositions according to the invention include anti-frizz polymers available for sale from Ashland Specialty Ingredients such as AquaStyle™ 300 and Styleze™ XT3. Information on related anti-frizz agents may be found in U.S. Pat. Nos. 7,914,773, 7,785,575, and U.S. published application 2010/00093584, the disclosures of each of which is hereby incorporated in its entirety by reference.

One or more plasticizers or coalescing agents may be added to modify the film forming characteristics of hair care compositions according to the invention. Non-limiting examples of plasticizers include glycols, adipic esters, phthalate esters, isobutyrate esters, terephthalate esters, epoxidized butyl esters or fatty acids, epoxidized vegetable oils, glycerine, di-2-ethylhexyladipate or dioctyladipate (DOA), di-2-ethylhexyl phthalate or dioctyl phthalate (DOP), di-2-ethylhexyl terephthalate (DOTP), dicyclohexyl phthalate, diisononyl adipate, diisononylphthalate, n-butyl benzyl phthalate, 1,3-butylene glycol/adipic acid polyester, dialkyl adipate, dialkyl phthalate derivatives where the alkyl group is a $C_1$-$C_{12}$ alkyl group, di-n-hexylazelate, diphenyl-phthalate, tricresol phosphate, benzyl benzoate, dibutyl phosphate, tributyl phosphate, tributoxyethyl phosphate, tri-phenyl phosphate, butyl acetyl ricinoleate, glycerol acetyl ricinoleate, dibutyl phthalate, diethyl phthalate, dioctyl phthalate, dimethoxyethyl phthalate, diisobutyl phthalate, diamyl phthalate, dibutyl glycolate, butyl stearate, triethyl citrate, tributyl citrate, tributyl acetyl citrate, 2-hexyltriethylacetyl citrate, dibutyl tartarate, camphor, epoxidized butyl esters of linseed oil fatty acids, epoxidized linseed oil, epoxidized soya oil, propylene glycol adipate, 2,2,4-trimethyl-1,3-pentanediol diisobutyrate (TXIB), methyl abietate, cumyl acetate, dibutoxyethyl adipate, di-n-hexylazalate, glyceryl-tri-benzerate, tri-n-butylcitrate, dioctyl fumarate, triisonyl trimellitate, dioctyl isophthalate, butyl oleate, chlorinated paraffin, tricresolphosphate, dibutyl sebacate, dimethicone copolyol (Dow Corning 190), PEG-6 capric/caprylic glyceride (SOFTIGEN 767), DIACETIN, LAURAMIDE DEA (MONAMID 716), phenyl trimethicone (ABIL AV 20-1000), propylene glycol, dipropylene glycol, as well as polymeric plasticizers, and mixtures thereof. Non-limiting examples of coalescing solvents include acetone, methyl acetate, and di- or tri-propylene glycol methyl ethers, and mixtures thereof. Further examples of plasticizers may be found in U.S. Pat. Nos. 5,753,216 and 5,676,935, the disclosures of each of which are hereby incorporated in its entirety by reference.

Non-limiting examples of propellants that may be used in hair care compositions of the invention include trichlorofluoromethane, chlorodifluoromethane, 1,1-difluoroethane, dichlorotetrafluoroethane, monochlorodifluoromethane, trichlorotrifluoroethane, dimethyl ether, $C_1$-$C_4$ hydrocarbons such as methane, ethane, propane, n-butane, and isobutane, water-soluble gases such as, dimethyl ether, carbon dioxide, and/or nitrous oxide, and insoluble, compressed gases such as nitrogen, helium, and fully-fluorinated oxetanes and oxepanes, and mixtures thereof.

Non-limiting examples of penetrants that may be used in hair care compositions of the invention include lanolin compounds, protein hydrolysates, protein derivatives, and mixtures thereof.

Non-limiting examples of anti-foaming agents that may be used in hair care compositions of the invention include carrier oils, silicone oils, silicone foam inhibitors, hydrophobic silica, hydrophobic fat derivatives, waxes, water-insoluble polymers, amphiphilic components, emulsifiers, coupling agents, and mixtures thereof.

Any known conditioning agent may be used in the personal care compositions of the invention. An extensive discussion on conditioning agents may be found in the book *Conditioning Agents for Skin and Hair, Cosmetic Science and Technology Series*, Volume 21, 1999, Marcel Dekker Publishers. The contents of the book are hereby incorporated in its entirety by reference.

Conditioning agents may be chosen from synthetic oils, mineral oils, vegetable oils, fluorinated or perfluorinated oils, natural or synthetic waxes, silicones, cationic polymers, proteins and hydrolyzed proteins, cationic surfactants, cer-amide type compounds, fatty amines, fatty acids and their derivatives, as well as mixtures of these different types of compounds.

Non-limiting examples of suitable synthetic oils include: polyolefins, e.g., poly-α-olefins, such as polybutenes, polyisobutenes, polydecenes, and blends thereof. The polyolefins may be hydrogenated.

Non-limiting examples of suitable mineral oils include hexadecane and oil of paraffin.

Non-limiting examples of suitable animal and vegetable oils include: sunflower oil, corn oil, soy oil, avocado oil, jojoba oil, squash oil, raisin seed oil, sesame seed oil, walnut oil, fish oil, glycerol tricaprocaprylate, purcellin oil, liquid jojoba, and blends thereof. Also suitable are natural oils such as oils of eucalyptus, lavender, vetiver, *Litsea cubeba*, lemon, sandalwood, rosemary, chamomile, savory, nutmeg, cinnamon, hyssop, caraway, orange, geranium, cade, bergamot, and blends thereof.

The conditioning agent may be a fluorinated or a perfluorinated oil. The fluoridated oils may also be fluorocarbons such as fluoramines, e.g., perfluorotributylamine, fluoridated hydrocarbons such as perfluorodecahydronaphthalene, fluoroesters, fluoroethers, and blends thereof.

Non-limiting examples of suitable natural and synthetic waxes include: carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The conditioning agent may be any silicone known by those skilled in the art. Silicones include polyorganosiloxanes that are insoluble in the composition. The silicones may be present in the form of oils, waxes, resins, or gums. They may be volatile or non-volatile.

Non-limiting examples of suitable silicones include: polyalkyl siloxanes, polyaryl siloxanes, polyalkyl aryl siloxanes, silicone gums and resins, polyorgano siloxanes modified by organofunctional groups, and blends thereof.

Suitable polyalkyl siloxanes include polydimethyl siloxanes with terminal trimethyl silyl groups or terminal dimethyl silanol groups (dimethiconol) and polyalkyl (C1-C20) siloxanes. Suitable polyalkyl aryl siloxanes include polydimethyl methyl phenyl siloxanes and polydimethyl diphenyl siloxanes. The siloxanes can have a linear or branched structure.

Suitable silicone gums include polydiorganosiloxanes, such as those having a number-average molecular weight between 200,000 Da and 1,000,000 Da used alone or mixed with a solvent.

Non-limiting examples of suitable silicone gums include: polymethyl siloxane, polydimethyl siloxane/methyl vinyl siloxane gums, polydimethyl siloxane/diphenyl siloxane, polydimethyl siloxane/phenyl methyl siloxane, polydimethyl siloxane/diphenyl siloxane/methyl vinyl siloxane, and blends thereof.

Non-limiting examples of suitable silicone resins include silicones with a dimethyl/trimethyl siloxane structure and resins of the trimethyl siloxysilicate type.

The organo-modified silicones suitable for use in the invention include silicones such as those previously defined and containing one or more organofunctional groups attached by means of a hydrocarbon radical, and grafted silicone polymers. The organo-modified silicones may be one from the amino functional silicone family.

The silicones may be used in the form of emulsions, nano-emulsions, or micro-emulsions.

The cationic polymers that may be used as conditioning agents according to the invention generally have a molecular weight (average number) from about 500 Da to about 5,000,000 Da, and particularly from about 1,000 Da to about 3,000,000 Da. The expression "cationic polymer" as used herein indicates any polymer having at least one cationic group.

The cationic polymers may be chosen from among polymers containing primary, secondary, tertiary amine, and/or quaternary ammonium groups that may form part of the main polymer backbone and/or side chain(s).

Non-limiting examples of suitable cationic polymers include polyamines, polyaminoamides, and quaternary polyammonium classes of polymers, such as:

(1) homopolymers and copolymers derived from acrylic or methacrylic esters or amides. The copolymers may contain one or more units derived from acrylamides, methacrylamides, diacetone acrylamides, acrylic or methacrylic acids or their esters, vinyllactams such as vinyl pyrrolidone or vinyl caprolactam, and vinyl esters. Non-limiting, specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone and dialkylaminoalkyl acrylate or methacrylate, optionally quaternized, such as the products sold under the name Gafquat™ by Ashland Specialty Ingredients; terpolymers of dimethyl amino ethyl methacrylate, vinyl caprolactam, and vinyl pyrrolidone such as the product sold under the name Gaffix™ VC 713 by Ashland Specialty Ingredients; the vinyl pyrrolidone/methacrylamidopropyl dimethylamine copolymer, marketed under the name Styleze™ CC 10 by Ashland Specialty Ingredients; and the vinyl pyrrolidone/quaternized dimethyl amino propyl methacrylamide copolymers such as the product sold under the name Gafquat™ HS 100 by Ashland Specialty Ingredients (Wayne, N.J.).

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as hydroxy alkyl cellulose, and hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups, and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalkylene polyamines with polycarboxylic acids followed by alkylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers include those described in U.S. Pat. Nos. 3,227,615 and 2,961,347.

(9) cyclopolymers of alkyl diallyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride.

(11) quaternary polyammonium polymers, including, for example, Mirapol® A 15, Mirapol® AD1, Mirapol® AZ1, and Mirapol® 175 products sold by Miranol.

(12) quaternary polymers of vinyl pyrrolidone and vinyl imidazole such as the products sold under the names Luviquat® FC 905, FC 550, and FC 370 by BASF Corporation.

(13) quaternary polyamines.

(14) reticulated polymers known in the art.

Other cationic polymers that may be used include cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

The conditioning agent may comprise a protein or hydrolyzed cationic or non-cationic protein. Non-limiting examples of suitable compounds include: hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one C1-C18 alkyl, and blends thereof.

Non-limiting examples of suitable hydrolyzed cationic proteins include: Croquat® L, in which the quaternary ammonium groups include a C12 alkyl group, Croquat® M, in which the quaternary ammonium groups include C10-C18 alkyl groups, Croquat® S in which the quaternary ammonium groups include a C18 alkyl group, Crotein® Q in which the quaternary ammonium groups include at least one C1-C18 alkyl group, and blends thereof. These products are sold by Croda.

The conditioning agent may also comprise quaternized vegetable protein(s) such as wheat, corn, or soy proteins, non-limiting examples of which include: cocodimonium hydrolyzed wheat protein, laurdimonium hydrolyzed wheat protein, steardimonium hydrolyzed wheat protein, 2-N-stearoyl amino-octadecane-1,3-diol, 2-N-behenoyl amino-octadec ane-1,3-diol, 2-N-[2-hydroxy-palmitoyl]-amino-octadec ane-1,3-diol, 2-N-stearoyl amino-octadec ane-1,3,4-triol, N-stearoyl phytosphingosine, 2-N-palmitoyl amino-hexadecane-1,3-diol, bis-(N-hydroxy ethyl N-cetyl) malonamide, N-(2-hydroxy ethyl)-N-(3-cetoxyl-2-hydroxy propyl) amide of cetylic acid, N-docosanoyl N-methyl-D-glucamine, and blends thereof.

The conditioning agent may also comprise a cationic surfactant such as a salt of a primary, secondary, or tertiary fatty amine, optionally polyoxyalkylenated, a quaternary ammonium salt, a derivative of imadazoline, or an amine oxide. Conditioning agents may also be selected from the group consisting of: mono-, di-, and tri-alkyl amines, and quaternary ammonium compounds with a counterion such as a chloride, a methosulfate, a tosylate, etc. Non-limiting examples of suitable amines include: cetrimonium chloride, dicetyldimonium chloride, behentrimonium methosulfate, and blends thereof.

The conditioning agent may comprise a fatty amine. Non-limiting examples of suitable fatty amines include: dodecyl amines, cetyl amines, stearyl amines such as stearamidopropyl dimethylamine, and blends thereof.

The conditioning agent may comprise a fatty acid or derivative(s) thereof. Non-limiting examples of suitable fatty acids include: myristic acid, palmitic acid, stearic acid, behenic acid, oleic acid, linoleic acid, isostearic acid, and blends thereof. The derivatives of fatty acids include carboxylic ester acids including mono-, di-, tri- and tetracarboxylic acids esters, amides, anhydrides, esteramides, imides, and mixtures of these functional groups.

Also suitable as conditioning agents are the following commercial products:

(1) Aquacat™ Clear Cationic Solution (INCI Name: guar hydroxypropyltrimonium Chloride), N-Hance™ SP-100 (INCI Name: acrylamidopropyl trimonium chloride/acrylamide copolymer), and N-Hance™ cationic guar (INCI Name: guar hydroxypropyltrimonium chloride) from Ashland Specialty Ingredients (2) Salcare® from BASF Corp.

(3) Softcat™ Polymers from The Dow Chemical Company.

(4) Jaguar® C500, Polycare® Boost, Mackconditioner™ Brite, and Mackine® 301 from Rhodia.

(5) Stepanquat® ML, Stepanquat® GA-90, Ninol®, and Ammonyx® from Stepan Company.

(6) Conditioneze™ 7 and Conditioneze™ NT-20 from Ashland Specialty Ingredients (Wayne, N.J.).

Of course, mixtures of two or more conditioning agents may be used.

The conditioning agent(s) may be present in an amount from about 0.001% to about 20%, particularly from about 0.01% to about 10%, and even more particularly from about 0.1% to about 3% by weight of the composition.

Personal care compositions may optionally comprise antimicrobial agent(s).

Non-limiting examples of suitable water insoluble, non-cationic antimicrobial agents include: halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, halogenated carbanilides, and blends thereof.

Non-limiting examples of suitable water soluble antimicrobial agents include: quaternary ammonium salts, bisbiquanide salts, triclosan monophosphate, and blends thereof.

The quaternary ammonium agents include those in which one or two of the substituents on the quaternary nitrogen has a carbon chain length (typically alkyl group) from about 8 to about 20, typically from about 10 to about 18 carbon atoms, while the remaining substituents (typically alkyl or benzyl group) have a lower number of carbon atoms, such as from about 1 to about 7 carbon atoms, typically methyl or ethyl groups.

Non-limiting examples of suitable quaternary ammonium antibacterial agents include: Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethyl-hexyl)-5-methyl hexahydropyrimidine, benzalkonium chloride, benzethonium chloride, methyl benzethonium chloride, and blends thereof.

Other antimicrobial compounds are bis[4-(R-amino)-1-pyridinium]alkanes as disclosed in U.S. Pat. No. 4,206,215. Other antimicrobials such as copper salts, zinc salts and/or stannous salts may also be included. Also useful are enzymes, including endoglycosidase, papain, dextranase, mutanase, and blends thereof. Such antimicrobial agents are disclosed in U.S. Pat. Nos. 2,946,725 and 4,051,234. The antimicrobial agents may also comprise chlorhexidine, triclosan, and flavor oils such as thymol. Triclosan and other agents are disclosed in U.S. Pat. Nos. 5,015,466 and 4,894,220.

In particular embodiments, one or more preservatives may be included.

Non-limiting examples of suitable preservatives include: benzoic acid, sorbic acid, dehydroacetic acid, diazolidinyl ureas, imidazolidinyl ureas, salicylic acid, piroctone olamine, DMDM hydantoin, IPBC (iodopropynyl butylcarbamate), triclosan, bronopol, formaldehyde, isothiazolinones, nitrates/nitrites, parabens, phenoxyethanol, potassium sorbate, sodium benzoate, sulphites, sulphur dioxide, and blends thereof.

In particular embodiments, preservative boosters/solvents may be incorporated, non-limiting examples of which include: caprylyl glycol, hexylene glycol, pentylene glycol, ethylhexylglycerin, caprylhydroxamic acid, caprylohydroxamic acid, glyceryl caprylate, and blends thereof.

Polysaccharides, such as gum Arabic, may be included as well.

Personal care compositions may comprise liquid or liquid-like carrier(s) that help to distribute, disperse, and/or dissolve the ingredients.

Non-limiting examples of suitable liquid carriers include: water, alcohols, oils, esters, and blends thereof.

The compositions of the invention may also be in the form of aqueous or hydro-alcoholic solutions.

The physiological and cosmetically acceptable medium may consist exclusively of water, a cosmetically acceptable solvent, or a blend of water and a cosmetically acceptable solvent, such as a lower alcohol composed of C1 to C4, such as ethanol, isopropanol, t-butanol, n-butanol, alkylene glycols such as propylene glycol, and glycol ethers.

In one of the embodiment, the compositions of the invention may be anhydrous.

Typically, sun care compositions may also comprise one or more UV actives, which include organic and inorganic materials that scatter, absorb, and/or reflect radiation having a wavelength from about 100 nm to about 400 nm.

In one particular embodiment, the sun care compositions protect against UV-A, UV-B, and/or UV-C radiation.

UV-A radiation, from about 320 nm to about 400 nm, has the longest wavelengths within the UV spectrum, and consequently is the least energetic. UV-A radiation includes UV-A1 (from about 340 nm to about 400 nm) and UV-A2 (from about 320 nm to about 340 nm). UV-B radiation has shorter wavelengths, from about 290 nm to about 320 nm. UV-C radiation has the shortest wavelengths from about 200 nm to about 290 nm.

In another embodiment, the sun care compositions may not contain UV actives, and may be regarded as tanning oils or tan promoters.

Sun care compositions may be formulated, for example, for application to the lips, hair, face, cheeks, neck, area around the eyes, full hands, and body area. Self-tanning compositions, which are products that color skin without requiring full sun exposure, also fit under the sun care umbrella.

Suitable UV absorber(s) that may be included in the personal care compositions most likely will depend on local regulations. As the rules governing the names and usage levels evolve over time, it is impossible to include every UV absorber that may be used with the invention.

Non-limiting examples of suitable UV absorbers include: octyl salicylate; pentyl dimethyl PABA; octyl dimethyl PABA; benzophenone-1; benzophenone-6; 2-(2H-benzotriazole-2-yl)-4,6-di-tert-pentylphenol; ethyl-2-cyano-3,3-diphenylacrylate; homomenthyl salicylate; bis-ethylhexyloxyphenol methoxyphenyl triazine; methyl-(1,2,2,6,6-pentamethyl-4-piperidyl)-sebacate; 2-(2H-benzotriazole-2-yl)-4-methylphenol; diethylhexyl butamido triazone; amyl dimethyl PABA; 4,6-bis(octylthiomethyl)-o-cresol; CAS number 65447-77-0; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol; 2-hydroxy-4-octyloxybenzophenone; benzophenone-2; diisopropyl methylcinnamate; PEG-PABA; 2-(1,1-dimethylethyl)-6-[[3-(1,1-demethylethyl)-2-hydroxy-5-methylphenyl]methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis[3-(3,5-di-tert-butyl-4-hydroxyphenylpropionamide)]; pentaerythritol tetrakis[3-(3,5-di-tert-butyl-4-hydroxyphenyl)propionate]; 2,6-di-tert-butyl-4-[4,6-bis(octylthio)-1,3,5-triazin-2-ylamino]phenol; 2-(2H-benzotriazole-2-yl)-4,6-bis(1-methyl-1-phenylethyl)phenol; trolamine salicylate; diethylanolamine p-methoxycinnamate; polysilicone-15; CAS number 152261-33-1; 4-methylbenzylidene camphor; bisoctrizole; N-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[(2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylendiamine; benzophenone-8; ethyl-4-bis(hydroxypropyl) aminobenzoate; 6-tert-butyl-2-(5-chloro-2H-benzotriazole-2-yl)-4-methylphenol; p-aminobenzoic acid; 3,3',3'',5,5',5''-hexa-tert-butyl-α-α'-α''-(mesitylene-2,4,6-triyl)tri-p-cresol; lawsone with dihydroxyacetone; benzophenone-9; benzophenone-4; ethylhexyl dimethoxy benzylidene dioxoimidazoline propionate; N,N'-bisformyl-N, N'-bis-(2,2,6,6-tetramethyl-4-piperidinyl)-; 3-benzylidene camphor; terephthalylidene dicamphor sulfonic acid; camphor benzalkonium methosulfate; bisdisulizole disodium; etocrylene; ferulic acid; 2-(2H-benzotriazole-2-yl)-4-(1,1,3, 3-tetramethylbutyl)-phenol; 4,6-bis(dodecylthiomethyl)-o-cresol; β-2-glucopyranoxypropyl hydroxy benzophenone; phenylbenzimidazole sulfonic acid; benzophenone-3; diethylamine hydroxybenzoyl hexylbenzoate; 3',3'-diphenylacryloyl)oxy]methyl}-propane; ethylhexyl p-methoxycinnamate, and blends thereof.

Personal care compositions may comprise antioxidant(s) and/or antiradical protecting agent(s).

Non-limiting examples of suitable antioxidants and/or antiradical protecting agents include: BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, lactoferrin, and blends thereof.

Personal care compositions may comprise vitamin(s), provitamin(s), and/or mineral(s).

Non-limiting examples of suitable vitamins include: ascorbic acid (vitamin C), vitamin E, vitamin E acetate, vitamin E phosphate, B vitamins such as B3 and B5, niacin, vitamin A, derivatives thereof, and blends thereof.

Non-limiting examples of suitable provitamins include: panthenol, retinol, and blends thereof.

Non-limiting examples of suitable minerals include: talc, clay, calcium carbonate, silica, kaolin, mica, and blends thereof. Further examples of minerals that may be used in the personal care compositions may be found in a brochure titled Minerals for Personal Care from Imerys Performance Minerals, the disclosure of which is hereby incorporated in its entirety by reference.

Personal care compositions may comprise one or more surfactants. Surfactants serve in solubilizing, dispersing, emulsifying and/or reducing the interfacial tension. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate.

Non-limiting examples of suitable cationic surfactants include: derivatives of aliphatic quaternary ammonium compounds having at least one long alkyl chain containing from about 8 to about 18 carbon atoms, such as, lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Further suitable are quaternary ammonium fluorides having detergent properties such as compounds described in U.S. Pat. No. 3,535,421. Certain cationic surfactants may act as germicides in the compositions disclosed herein.

Nonionic surfactants useful herein include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Also suitable as surfactants are the following commercial products:

(1) Alkanolamides, under the trade names Amidex™ and Schercomid™; amido-amines, under the trade names Katemul™ and Schercodine™; amine oxides, under the trade names Chemoxide™ and Schercamox™; amphoterics, under the trade names Chembetaine™, Schercotaine™ and Schercoteric™; imidazolines, under the trade name Schercozoline™; pearlizing agents, under the trade name Quickpearl™; performance concentrates, under the trade names Sulfochem™ and Chemoryl™; soaps (potassium cocoate and potassium soyate); specialty ethoxylates, under the trade name Chemonic™; specialty quats under the trade names Quatrex™ and Schercoquat™; sulfates, under the trade name Sulfochem™; and sulfosuccinates, under the trade name Chemccinate™ from Lubrizol.

(2) Avaniel, Cremaphore®, Jordapan®, and Pluracare® from BASF Corp.

(3) Miracare® SLB, Mackam® Bab, Mackanate® Ultra SI, Miranol® Ultra, and Miracare® Plaisant from Rhodia.

(4) Stepan® Pearl 2, Stepan® Pearl 4, Stepan® Pearl Series, Neobee® M-20, Stepan® PTC, Amphosol® 2CSF, Steol®, Stepan-Mild® GCC, Stepan® SLL-FB, Stepanol® AM, Stepanol® PB, Alpha-Step® BSS-45, Bio-Terge® 804, Stepan-Mild® L3, Stepan® SLL-FB, Stepan® SSL-CG, and Stepanol® CFAS-70 from Stepan Company.

Also suitable as surfactants are those described in the book *Surfactants in Personal Care Products and Decorative Cosmetics*, Third Edition, 2006, CRC Press. The disclosure is incorporated hereby in its entirety by reference.

Personal care compositions may be also be formulated as detergent compositions, such as shampoos, bath gels, and bubble baths. Such compositions comprise water as a liquid carrier. The surfactant or surfactants that form the washing base may be chosen alone or in blends, from known anionic, amphoteric, zwitterionic and/or non-ionic surfactants. The quantity and quality of the washing base must be sufficient to impart a satisfactory foaming and/or detergent value to the final composition. The washing base may be present in an amount from about 4% to about 50% by weight, particularly from about 6% to about 35% by weight, and more particularly from about 8% to about 25% by weight of the final composition.

Personal care compositions may comprise one or more thickener(s) and/or viscosifier(s).

Non-limiting examples of suitable thickeners and/or viscosifiers include: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *Arachis hypogaea* (peanut) flour; ascorbyl methylsilanol pectinate; astragalus gummifer gum; attapulgite; *Avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; *Caesalpinia spinosa* gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; *Ceratonia siliqua* gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus *Aurantium dulcis* (orange) peel extract; cocamide DEA; cocamide MEA; cocamide MIPA; cocamidoethyl betaine; cocamidopropyl betaine; cocamidopropyl hydroxysultaine; cocobetaine; coco-hydroxysultaine; coconut alcohol; coco/oleamidopropyl betaine; coco-Sultaine; cocoyl sarcosinamide DEA; comamide/cocamide DEA; comamide DEA; croscarmellose; crosslinked bacillus/glucose/sodium glutamate ferment; *Cyamopsis tetragonoloba* (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 cros spolymer; dimethicone/PEG-15 cros spolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; *Glycine soja* (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/™MG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/™MG copolymer; PEG-150 pentaerythrityl tetrastearate; PEG-4 rapeseedamide; PEG-150/stearyl alcohol/SMDI copolymer; *Phaseolus angularis* seed powder; *Polianthes tuberosa* extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *Pyrus cydonia* seed; *Pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *Rosa multiflora* flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *Solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; *Sterculia urens* gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *Triticum vulgare* (wheat) germ powder; *Triticum vulgare* (wheat) kernel flour; *Triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; *Zea mays* (corn) starch; and blends thereof.

Also suitable as thickeners and/or viscosifiers are the following commercial products:

(1) Aqualon™ carboxymethylcellulose, Benecel™ methylcellulose and hydroxypropyl methylcellulose, Blanose™ sodium carboxymethylcellulose, Klucel™ hydroxypropylcellulose, Natrosol™ hydroxyethylcellulose, Natrosol™ Plus and PolySurf™ cetyl modified hydroxyethylcellulose, N-Hance™ cationic guar, N-Hance™ HP Series hydroxypropyl guar, N-Hance™ SP-100 conditioning polymer, and Supercol™ guar gum from Ashland Specialty Ingredients (2) Carbopol® Polymers, Fixate™ PLUS Polymer, Glucamate™ Thickeners, Amidex™ Surfactants, Chembetaine™ Surfactants, Chemoxide™ Surfactants, Chemonic™ Surfactants, Chemccinate™ Surfactants, Amidex™ BC-24 Surfactant, Chemoryl™ LB-30 Surfactant, Novethix™ L-10 Polymer, Ceralan™ Lanolin Product, Pemulen™ TR-1 Polymeric Emulsifier, Pemulen™ TR-2 Polymeric Emulsifier, Hydramol™ PGPD Ester, Schercodine™ M Amido-Amine, Schercodine™ P Amido-Amine, Schercomid™ Diethanolamides from The Lubrizol Corporation.

(3) Salcare® and Luvigel® from BASF Corporation.

(4) Aculyn™ 22, Aculyn™ 28, Aculyn™ 33, Aculyn™ 38, and Aculyn™ 44 from The Dow Chemical Company.

(5) Ammonyx® C and Stepan-Mild® GCC from Stepan Company.

(6) Stabileze™, Rapithix™ A-60, Rapithix™ A-100, Ultrathix™ P-100, Lubrajel™ and FlexiThix™ from Ashland Specialty Ingredients (Wayne, N.J.).

Also suitable as a thickener/rheology modifier are lightly- to moderately-crosslinked polyvinylpyrrolidones. Disclosures of these polymers are provided in the following publications, each of which is hereby incorporated in its entirety by reference: U.S. Pat. Nos. 5,073,614; 5,312,619; 5,139,770; 5,716,634; 5,470,884; 5,759,524; 5,997,887; 6,024,942; as well as international application PCT/US10/26973, PCT/US10/26976, PCT/US10/26940, PCT/US11/32993, and PCT/US11/34515.

Personal care compositions may comprise natural extracts and/or natural products. Extensive details on natural products that can be used in personal care compositions is provided in book chapter "Chemistry of Cosmetics, Comprehensive Natural Products II" in *Chemistry and Biology*; volume 3, 2010.

Oral Care Composition Ingredients

Oral care compositions may optionally contain one or more additional ingredients. Non-limiting examples of suitable ingredients include: carriers, dentifrices, cleaning agents, breath freshening actives, pain relievers, anesthetics, anti-inflammatory agents, antimicrobial agents, antibacterial agents, anti-calculus agents, anti-plaque agents, gums, thickeners, gelling agents, surfactants, flavors, warming or tingling agents, tooth bleaching agents, whiteners, stain removers, stain preventers, abrasives, adhesives, colors, emollients, emulsifiers, preservatives, solvents, binders, stimulants, depressants, diet aids, smoking cessation aides, vitamins, minerals, throat-soothing agents, spices, herbs, herbal extracts, alkaloids (such as caffeine and nicotine), and humectants.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, as disclosed in e.g., U.S. Pat. No. 3,988,433. Carrier materials for biphasic dentifrice formulations are disclosed in U.S. Pat. Nos. 5,213,790; 5,145,666; 5,281,410; 4,849,213; and 4,528,180. Mouthwash, rinse or mouth spray carrier materials typically include water, flavoring and sweetening agents, etc., as disclosed in, e.g., U.S. Pat. No. 3,988,433. Lozenge carrier materials typically include a candy base; chewing gum carrier materials include a gum base, flavoring and sweetening agents, as in, e.g., U.S. Pat. No. 4,083,955. Sachet carrier materials typically include a sachet bag, flavoring and sweetening agents. For sub-gingival gels used for delivery of actives into the periodontal pockets or around the periodontal pockets, a "sub-gingival gel carrier" is chosen as disclosed in, e.g., U.S. Pat. Nos. 5,198,220 and 5,242,910. The selection of a carrier will depend on secondary considerations like taste, cost, and shelf stability, and other factors.

Oral care compositions may comprise one or more dental abrasives. Dental abrasives useful in the compositions include many different materials. The material selected must be one which is compatible within the composition of interest and does not excessively abrade dentin.

Non-limiting examples of suitable abrasives include: silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, resinous abrasive materials such as particulate condensation products of urea and formaldehyde, and blends thereof.

Another class of abrasives is the particulate thermosetting synthesized resins as described in U.S. Pat. No. 3,070,510.

Non-limiting examples of suitable resins include: melamines, phenolics, ureas, melamine-ureas, melamine-formaldehydes, urea-formaldehyde, melamine-urea-formaldehydes, cross-linked epoxides, cross-linked polyesters, and blends thereof.

Silica dental abrasives of various types may be employed because of their unique benefits of exceptional dental cleaning and polishing performance without unduly abrading tooth enamel or dentine. The silica abrasive polishing materials herein, as well as other abrasives, generally have an average particle size ranging from about 0.1 to about 30 microns, and particularly from about 5 to about 15 microns. The abrasive can be precipitated silica or silica gels such as the silica xerogels described in U.S. Pat. Nos. 3,538,230, and 3,862,307.

Non-limiting examples of suitable silica abrasives include: silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the invention are described in more detail in U.S. Pat. Nos. 4,340,583; 5,603,920; 5,589,160; 5,658,553; 5,651,958; and 6,740,311. Each of these disclosures is hereby incorporated in its entirety by reference.

Mixtures of abrasives can be used such as mixtures of the various grades of Zeodent® silica abrasives listed above.

The total amount of abrasive(s) in the oral care compositions typically range from about 6% to about 70% by weight; toothpastes may contain from about 10% to about 50% of abrasives by weight of the composition. Dental solution, mouth spray, mouthwash and non-abrasive gel compositions typically contain little or no abrasives.

Oral care compositions may comprise polymeric mineral surface active agent(s) (PMSAs). PMSAs include any agent which will have a strong affinity for the tooth surface, deposit a polymer layer or coating on the tooth surface and produce the desired surface modification effects. The "mineral" descriptor is intended to convey that the surface activity or substantivity of the polymer is toward mineral surfaces such as calcium phosphate minerals or teeth.

Non-limiting examples of suitable PMSAs include: polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate), poly(vinyl benzyl chloride), polycarboxylates, carboxy-substituted polymers, and blends thereof. Also suitable as polymeric mineral surface active agents are the carboxy-substituted alcohol polymers described in U.S. Pat. Nos. 5,292,501; 5,213,789, 5,093,170; 5,009,882; and 4,939,284; and the diphosphonate-derivatized polymers in U.S. Pat. No. 5,011,913; the synthetic anionic polymers including polyacrylates and copolymers of maleic anhydride or acid and methyl vinyl ether (e.g., Gantrez®), as described, for example, in U.S. Pat. No. 4,627,977. Another example of a polymeric mineral surface active agent is a diphosphonate modified polyacrylic acid.

Polymers with activity must have sufficient surface binding propensity to desorb pellicle proteins and remain affixed to enamel surfaces. For tooth surfaces, polymers with end or side chain phosphate or phosphonate functions may be used, although other polymers with mineral binding activity may prove effective depending upon adsorption affinity.

PMSAs are useful in the compositions because of their stain prevention benefit. It is believed the PMSAs provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSAs on teeth can also prevent stains from accruing due to disruption of binding sites of color bodies on tooth surfaces.

The ability of PMSA to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers. The desired surface effects may include: 1) creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

Oral care compositions may comprise additional anticalculus agent(s), such as a pyrophosphate salt as a source of pyrophosphate ion.

Non-limiting examples of suitable pyrophosphate salts include: dialkali metal pyrophosphate salts, tetraalkali metal pyrophosphate salts, and mixtures thereof. Particularly, disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms may find utility.

In compositions of the invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, particularly from about 1.5% to about 10%, and more particularly from about 2% to about 6%. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, particularly less than about 10% of the total pyrophosphate dissolved in the composition. Tetrasodium pyrophosphate salt may be one such pyrophosphate salt in these compositions. Tetrasodium pyrophosphate may be the anhydrous salt form or the decahydrate form, or any other species stable in solid form in the oral care compositions. The salt is in its solid particle form, which may be its crystalline and/or amorphous state, with the particle size of the salt being small enough to be aesthetically acceptable and readily soluble during use. The amount of pyrophosphate salt useful in making these compositions is any tartar control effective amount, generally from about 1.5% to about 15%, particularly from about 2% to about 10%, and more particularly from about 3% to about 8% by weight of the oral care composition.

The pyrophosphate salts are described in more detail in *Kirk-Othmer Encyclopedia of Chemical Technology*, third edition, volume 17, Wiley-Interscience Publishers (1982).

Oral care compositions may comprise peroxide compounds.

Non-limiting examples of suitable peroxide compounds include: hydrogen peroxide and organic peroxides including urea peroxide, carbamide peroxide, glyceryl peroxide, benzoyl peroxide, derivatives thereof, and blends thereof.

Typically, the peroxide compound can be employed in amounts so that at least about 1% by weight of the composition comprises peroxide. The peroxide compound may comprise from about 2% to about 30% by weight of the composition. More particularly, the peroxide comprises from about 3% to about 15% by weight of the composition. A typical peroxide concentration in the composition is generally from about 2% to about 7% by weight for home use products, and from about 15% to about 20% by weight for dental professional use.

Thickening or gelling agents used in dentifrice compositions may include nonionic polyoxyethylene polyoxypropylene block copolymers. Illustrative of polyoxyethylene polyoxypropylene block copolymers useful in the practice include block copolymers having the formula $HO(C_2H_4O)_b(C_3H_6O)_a(C_2H_4O)_bH$ wherein a is an integer such that the hydrophobic base represented by $(C_3H_6O)$ has a molecular weight of about 2,750 Da to 4000 Da, b is an integer such that the hydrophilic portion (moiety) represented by $(C_2H_4O)$ constitutes from about 70% to about 80% by weight of the copolymer. Block copolymers of this composition are available commercially under the trademark Pluronic® F type.

Pluronic® F127 has a molecular weight of 4,000 Da and contains 70% of the hydrophilic polyoxyethylene moiety.

Also suitable as a thickening agent is lightly- to moderately-crosslinked PVP, described in international application PCT/US11/30642.

The thickening agents may be present in an amount from about 15% to about 50% by weight, particularly from about 25% to about 45% by weight of the composition.

Surfactants may also be included in the oral care compositions of the invention, where they may serve in solubilizing, dispersing, emulsifying and/or reducing the surface tension of the teeth in order to increase the contact between the tooth and the peroxide. The compositions may also comprise surfactants, also commonly referred to as sudsing agents. Suitable surfactants are those which are reasonably stable and foam throughout a wide pH range. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type. Many suitable anionic surfactants are disclosed in U.S. Pat. No. 3,959,458. The compositions may comprise an anionic surfactant in an amount from about 0.025% to about 9% by weight, particularly from about 0.05% to about 5% by weight, and more particularly from about 0.1% to about 1% by weight of the composition.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate. The sarcosinate surfactant may be present in the compositions from about 0.1% to about 2.5%, particularly from about 0.5% to about 2.0% by weight of the total composition.

Non-limiting examples of suitable cationic surfactants include: derivatives of aliphatic quaternary ammonium compounds having at least one long alkyl chain containing from about 8 to about 18 carbon atoms such as lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Also suitable are the quaternary ammonium fluorides described in U.S. Pat. No. 3,535,421, where the quaternary ammonium fluorides have detergent properties. Certain cationic surfactants can also act as germicides in the compositions disclosed herein.

Nonionic surfactants that may be used in the compositions of the invention include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Oral care compositions may comprise flavor(s).

Non-limiting examples of suitable flavors include: methyl salicylate, ethyl salicylate, methyl cinnamate, ethyl cinnamate, butyl cinnamate, ethyl butyrate, ethyl acetate, methyl anthranilate, iso-amyl acetate, iso-armyl butyrate, allyl caproate, eugenol, eucalyptol, thymol, cinnamic alcohol, cinnamic aldehyde, octanol, octanal, decanol, decanal, phenylethyl alcohol, benzyl alcohol, benzaldehyde, α-terpineol, linalool, limonene, citral, vanillin, ethyl vanillin, propenyl guaethol, maltol, ethyl maltol, heliotropin, anethole, dihydroanethole, carvone, oxanone, menthone, β-damascenone, ionone, gamma decalactone, gamma nonalactone, gamma undecalactone, 4-hydroxy-2,5-dimethyl-3(2H)-furanone, and blends thereof.

Generally suitable flavoring agents are those containing structural features and functional groups that are less prone to oxidation by peroxide. These include derivatives of flavor chemicals that are saturated or contain stable aromatic rings or ester groups.

Also suitable are flavor chemicals that may undergo some oxidation or degradation without resulting in a significant change in the flavor character or profile. The flavor chemicals, including menthol, may be provided as single or purified chemicals rather than supplied in the composition by addition of natural oils or extracts such as peppermint, spearmint, or wintergreen oils as these sources may contain other components that are relatively unstable and may degrade in the presence of peroxide. Flavoring agents are generally used in the compositions at levels of from about 0.001% to about 5% by weight of the composition.

The flavor system may typically include sweetening agent(s). Sweeteners include compounds of natural and artificial origin.

Non-limiting examples of suitable water-soluble natural sweeteners include: monosaccharides, disaccharides and polysaccharides, such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and blends thereof.

Non-limiting examples of suitable water-soluble artificial sweeteners include: soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-α-aspartyl-N-

(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, derivatives thereof, and blends thereof. Water-soluble sweeteners derived from naturally occurring water-soluble sweeteners, such as a chlorinated derivative of ordinary sugar (sucrose), known, for example, under the product description of sucralose as well as protein based sweeteners such as *Thaumatoccous danielli* (Thaumatin I and II) may be used. The compositions may contain sweetener(s) in an amount from about 0.1% to about 10% by weight, in particular from about 0.1% to about 1% by weight of the composition.

In addition, the flavor system may include salivating agents, warming agents, and numbing agents. These agents are present in the compositions in an amount from about 0.001% to about 10% by weight, particularly from about 0.1% to about 1% by weight of the composition.

A non-limiting example of suitable salivating agent includes Jambus® manufactured by Takasago. Non-limiting examples of suitable warming agents include capsicum and nicotinate esters such as benzyl nicotinate. Non-limiting examples of suitable numbing agents include benzocaine, lidocaine, clove bud oil, ethanol, and blends thereof.

Oral care compositions may comprise chelating agent(s).

The chelating agents may include metal solubilizing agents and metal precipitating agents. The metal solubilizing agents include a condensed pyrophosphate compound. For purposes of this invention "condensed phosphate" relates to an inorganic phosphate composition containing two or more phosphate species in a linear or cyclic pyrophosphate form. The condensed phosphate may be sodium pyrophosphate, but may also include tripolyphosphate, hexametaphosphate, cyclic condensed phosphate or other similar phosphates well known in the field. The blend may also include an organic chelating agent. The term "organic phosphate" includes phosphonic acid, di and tri phosphonoc acid compound or its salts. An example of phosphonic acid is 1-hydroxyethylidene-1,1-diphosphonic acid that is sold under the trade name of Dequest®. The blend may also include a metal precipitating chelating agent. The term "metal precipitating chelating agent" is an agent that binds to metals and causes the metal to precipitate and includes halogens such as fluoride. The chelating agents are incorporated in the oral care compositions of the invention in an amount from about 0.1% to about 8.0% by weight, and particularly from about 0.5% to about 3.0% by weight of the composition, in a ratio of about 3:1:1 w/w organic chelating agent: condensed phosphate chelating agent: metal precipitating agent.

Another optional ingredient that may be used in oral care compositions is a humectant. For example, a humectant may be added to keep toothpaste compositions from hardening upon exposure to air, to give compositions a moist feel to the mouth, and, for particular humectants, to impart desirable sweetness of flavor to toothpaste compositions. The humectant, on a pure humectant basis, is generally present from about 0% to about 70%, particularly from about 5% to about 25% by weight of the composition.

Non-limiting examples of suitable humectants include: edible polyhydric alcohols such as glycerin, sorbitol, xylitol, butylene glycol, polyethylene glycol, propylene glycol, trimethyl glycine, and blends thereof.

The invention also contemplates oral care compositions comprising polymer(s) described herein complexed with hydrogen peroxide. A description of such complexes is present in international application WO 91/07184, the contents of which are hereby incorporated in their entirety by reference.

Also contemplated are oral care compositions such as those described in the following patents and patent applications, the contents of each are hereby incorporated in their entirety by reference: WO 2011/068514, WO 2011/053877, US 2010/0275394, US 2011/0076090, US 2008/091935, US 2008/0181716, US 2008/0014224, WO 2007/066837, US 2008/0292669, US 2007/0071696, US 2007/0154863, US 2008/0317797, US 2005/0249678, US 2007/0178055, US 2007/0189983, WO 2005/041910, U.S. Pat. No. 7,785,572, WO 1998/005749, WO 1997/022651, and U.S. Pat. No. 5,310,563.

Oral care compositions may comprise one or more denture adhesives.

Synthetic materials presently dominate the denture adhesive market. Such materials may consist of mixtures of the salts of short-acting polymers (e.g., carboxymethylcellulose or "CMC") and long-acting polymers (e.g., poly[vinyl methyl ether maleate], or "Gantrez" and its salts). Polyvinylpyrrolidone (povidone) may also be used.

Other components of denture adhesive products impart particular physical attributes to the formulations. Petrolatum, mineral oil, and polyethylene oxide may be included in creams to bind the materials and to make their placement easier. Silicon dioxide and calcium stearate may be used in powders to minimize clumping. Menthol and peppermint oils may be used for flavoring, red dye for color, and sodium borate and methyl- or poly-paraben as preservatives.

It is also contemplated that the composition ingredients may be formulated in a single container, or the ingredients may be formulated in-part in two or more distinct containers of the same or different type, the contents of which may require mixing prior to use.

The compounds, polymers, and non-homopolymers according to the invention may be prepared according to the examples set out below. The examples are presented for purposes of demonstrating, but not limiting, the preparation of the compounds, polymers, and non-homopolymers according to the invention.

EXAMPLES

Example 1: Synthesis of Poly(25.0% VP-25.0% AA-25.0% MMA-12.5% IBM-12.5% DIBF)

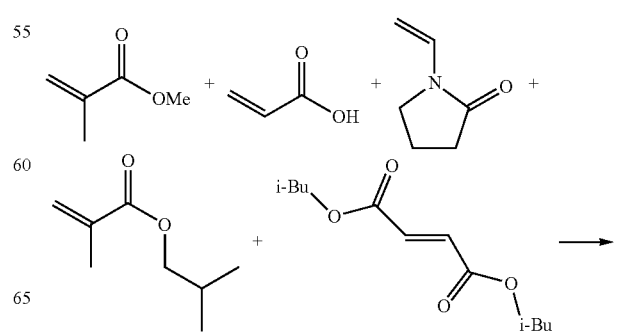

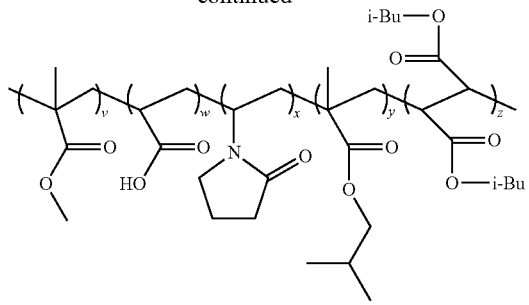

A 1-L jacketed glass reactor was loaded with t-butanol (280.0 g). A monomer solution of N-vinyl-2-pyrrolidone (47.42 g), acrylic acid (30.78 g), diisobutyl fumarate (48.72 g), methyl methacrylate (42.74 g) and isobutyl methacrylate (30.34 g) was prepared and charged into a syringe pump. Then, 33.3% of the monomer solution was charged into the reactor. The mixture in the reactor was de-aerated and heated to 68° C. under nitrogen with mechanical stirring at 200 rpm. At t=0, t-butyl peroxypivalate initiator (Trigonox® 25-C75, Akzo Nobel) (0.32 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.32 g each). The reaction temperature then was raised to 76° C. at t=4 hour and additional initiator was charged at t=5, 8 and 10 hour (0.85 g each). After the last initiator addition, stirring continued at 76° C. for 4 hours. After cooling, a viscous copolymer solution was discharged into a glass bottle.

Example 2: Synthesis of Synthesis of Poly(25.0% VP-25.0% AA-25.0% MMA-12.5% IBM-12.5% DIBF)

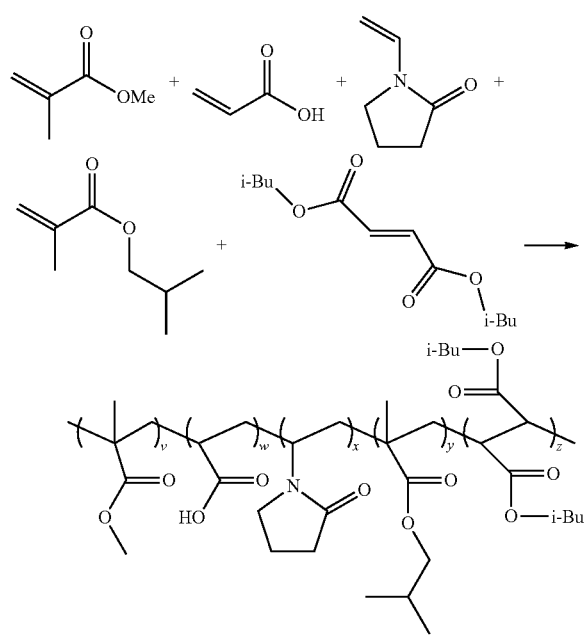

An autoclave reactor was loaded with t-butanol (238.5 g). A monomer solution of N-vinyl-2-pyrrolidone (42.68 g), acrylic acid (27.70 g), diisobutyl fumarate (43.85 g), methyl methacrylate (38.47 g) and isobutyl methacrylate (27.30 g) was prepared and charged into a syringe pump. Then, 25.0% of the monomer solution was charged into the reactor. The mixture in the reactor was de-aerated and heated to 68° C. under nitrogen with mechanical stirring at 200 rpm. At t=0, t-butyl peroxypivalate initiator (Trigonox® 25-C75, Akzo Nobel) (0.29 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.29 g each). The reaction temperature then was raised to 76° C. at t=4 hour and additional initiator was charged at t=5, 8 and 10 hour (0.77 g each). After the last initiator addition, stirring continued at 76° C. for 4 hours. After cooling, a viscous copolymer solution was discharged into a glass bottle.

Example 3: Synthesis of Synthesis of Poly(25.0% VP-25.0% AA-25.0% MMA-12.5% IBM-12.5% DIBF)

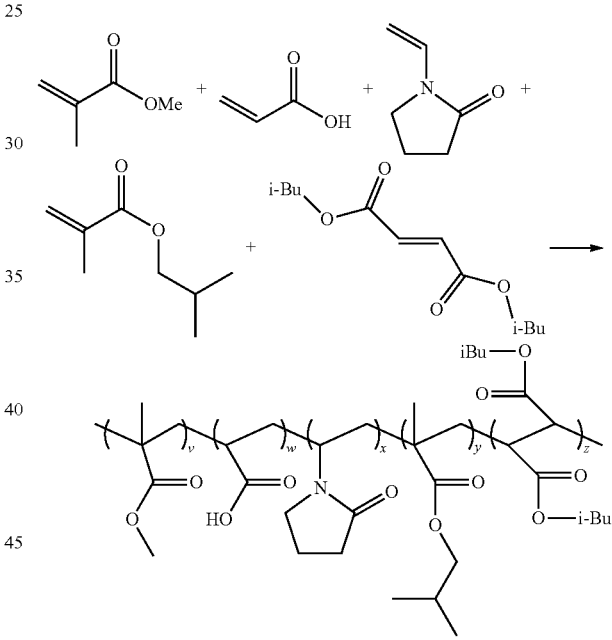

An autoclave reactor was loaded with t-butanol (238.0 g). A monomer solution of N-vinyl-2-pyrrolidone (42.68 g), acrylic acid (27.70 g), diisobutyl fumarate (43.85 g), methyl methacrylate (38.47 g) and isobutyl methacrylate (27.30 g) was prepared and charged into a syringe pump. Then, 20.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.29 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.29 g each). The reaction temperature then was raised to 76° C. at t=5 hour and additional initiator was charged at t=6, 9 and 11 hour (0.77 g each). After the last initiator addition, stirring continued at

Example 4: Synthesis of Synthesis of Poly(25.0% VP-25.0% AA-25.0% MMA-12.5% IBM-12.5% DIBF)

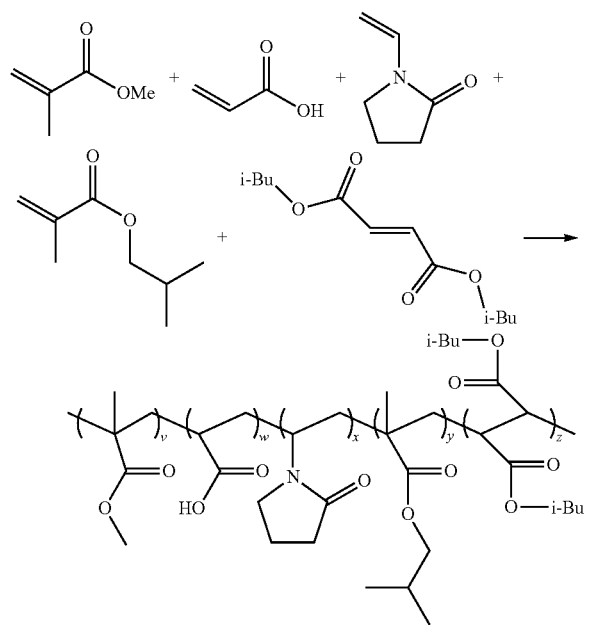

A 1-L jacketed glass reactor was loaded with t-butanol (238.0 g). A monomer solution of N-vinyl-2-pyrrolidone (42.68 g), acrylic acid (27.70 g), diisobutyl fumarate (43.85 g), methyl methacrylate (38.47 g) and isobutyl methacrylate (27.30 g) was prepared and charged into a syringe pump. Then, 20.0% of the monomer solution was charged into the reactor. The mixture in the reactor was de-aerated and heated to 69° C. under nitrogen with mechanical stirring at 200 rpm. At t=0, t-butyl peroxypivalate initiator (Trigonox® 25-C75, Akzo Nobel) (0.48 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.48 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

Example 5: Synthesis of Synthesis of Poly(25.0% VP-25.0% AA-25.0% MMA-12.5% IBM-12.5% DIBF)

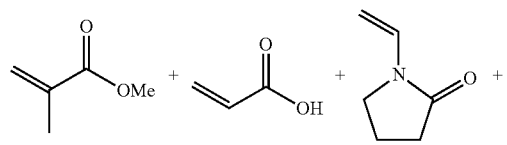

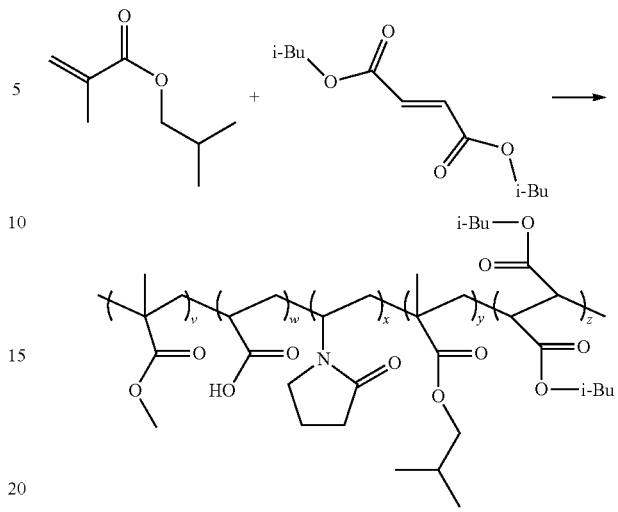

A 1-L jacketed glass reactor was loaded with t-butanol (238.0 g). A monomer solution of N-vinyl-2-pyrrolidone (42.68 g), acrylic acid (27.70 g), diisobutyl fumarate (43.85 g), methyl methacrylate (38.47 g) and isobutyl methacrylate (27.30 g) was prepared and charged into a syringe pump. Then, 20.0% of the monomer solution was charged into the reactor. The mixture in the reactor was de-aerated and heated to 68° C. under nitrogen with mechanical stirring at 200 rpm. At t=0, t-butyl peroxypivalate initiator (Trigonox® 25-C75, Akzo Nobel) (0.58 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.58 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

Example 6: Synthesis of Synthesis of Poly(25.0% VP-25.0% AA-25.0% MMA-12.5% IBM-12.5% DIBF)

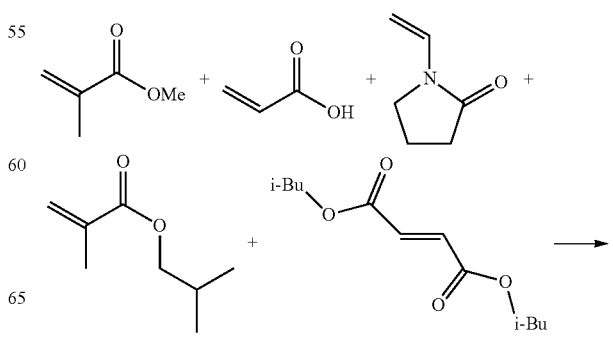

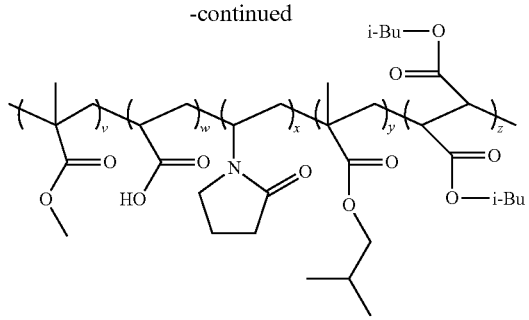

A 1-L jacketed glass reactor was loaded with t-butanol (238.0 g). A monomer solution of N-vinyl-2-pyrrolidone (42.68 g), acrylic acid (27.70 g), diisobutyl fumarate (43.85 g), methyl methacrylate (38.47 g) and isobutyl methacrylate (27.30 g) was prepared and charged into a syringe pump. Then, 10.0% of the monomer solution was charged into the reactor. The mixture in the reactor was de-aerated and heated to 68° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

Example 7: Synthesis of Synthesis of Poly(25.0% VP-25.0% AA-25.0% MMA-12.5% IBM-12.5% DIBF)

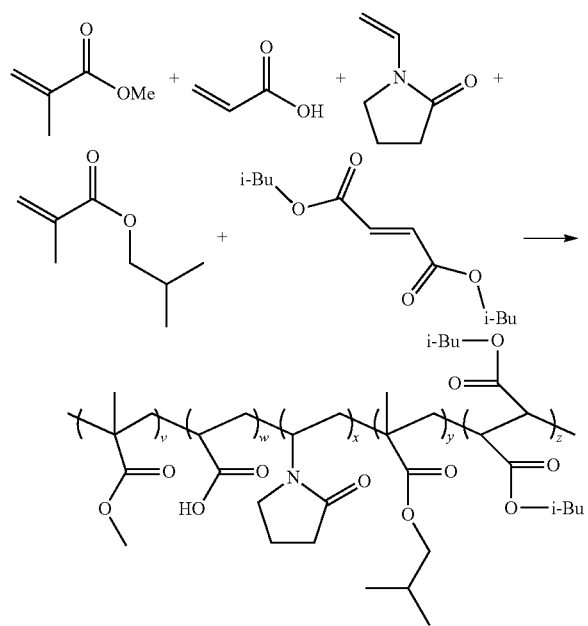

A 1-L jacketed glass reactor was loaded with t-butanol (238.0 g). A monomer solution of N-vinyl-2-pyrrolidone (42.68 g), acrylic acid (27.70 g), diisobutyl fumarate (43.85 g), methyl methacrylate (38.47 g) and isobutyl methacrylate (27.30 g) was prepared and charged into a syringe pump. Then, 15.0% of the monomer solution was charged into the reactor. The mixture in the reactor was de-aerated and heated to 68° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

This polymer was dried from solution, and the molecular weight was measured using gel permeation chromatography with poly(ethylene oxide) standards. The weight-average molecular weight ($M_w$) was found to be 105,000 Da, and the number-average molecular weight 18,500 Da.

Additionally, the acid number was found to be 112.13 mg KOH/g or 1.9988 meq/g.

Example 8: Synthesis of Synthesis of Poly(25.0% VP-25.0% AA-25.0% MMA-12.5% IBM-12.5% DIBF)

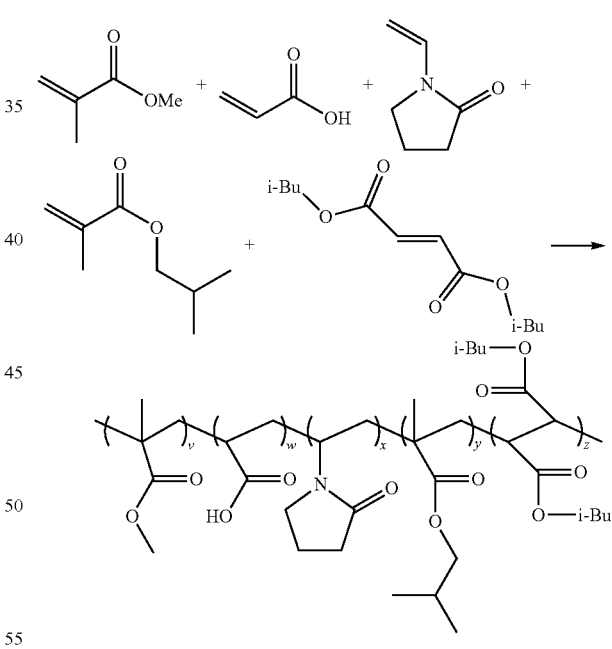

An autoclave reactor was loaded with t-butanol (238.0 g). A monomer solution of N-vinyl-2-pyrrolidone (42.68 g), acrylic acid (27.70 g), diisobutyl fumarate (43.85 g), methyl methacrylate (38.47 g) and isobutyl methacrylate (27.30 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 77° C. at t=5 hour and additional initiator was charged at t=6, 9 and 11 hour (0.72 g each). After the last initiator addition, stirring continued at 77° C. for 4 hours. After cooling, a viscous copolymer solution was discharged into a glass bottle.

This polymer was dried from solution, and the molecular weight was measured using gel permeation chromatography with poly(ethylene oxide) standards. The weight-average molecular weight ($M_w$) was found to be 119,900 Da, and the number-average molecular weight 24,400 Da.

The acid number was found to be 113.36 mg KOH/g or 2.0208 meq/g.

Example 9: Synthesis of Synthesis of Poly(25.0% VP-25.0% AA-25.0% MMA-12.5% IBM-12.5% DIBF)

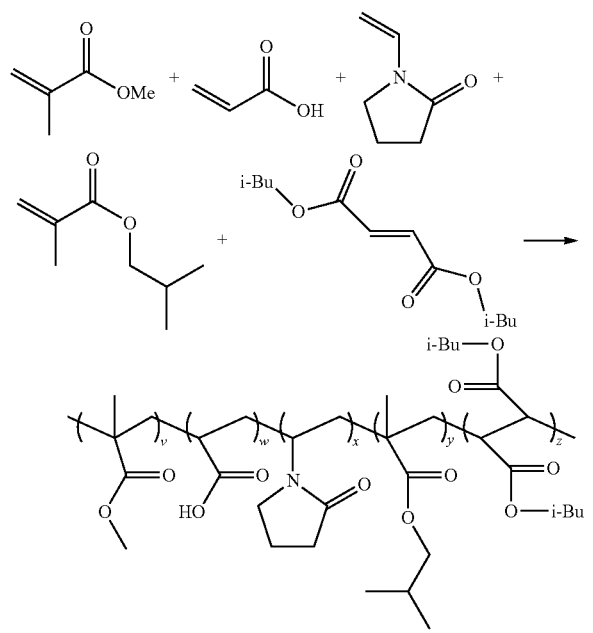

A 1-L jacketed glass reactor was loaded with t-butanol (238.0 g). A monomer solution of N-vinyl-2-pyrrolidone (42.68 g), acrylic acid (27.70 g), diisobutyl fumarate (43.85 g), methyl methacrylate (38.47 g) and isobutyl methacrylate (27.30 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 77° C. at t=5 hour and additional initiator was charged at t=6, 9 and 11 hour (0.72 g each). After the last initiator addition, stirring continued at 77° C. for 4 hours. After cooling, a viscous copolymer solution was discharged into a glass bottle.

This polymer was dried from solution, and the molecular weight was measured using gel permeation chromatography with poly(ethylene oxide) standards. The weight-average molecular weight ($M_w$) was found to be 90,200 Da, and the number-average molecular weight 16,900 Da.

The acid number was found to be 112.97 mg KOH/g or 2.0137 meq/g.

Example 10: Synthesis of Synthesis of Poly(25.0% VP-25.0% AA-25.0% MMA-12.5% IBM-12.5% DIBF)

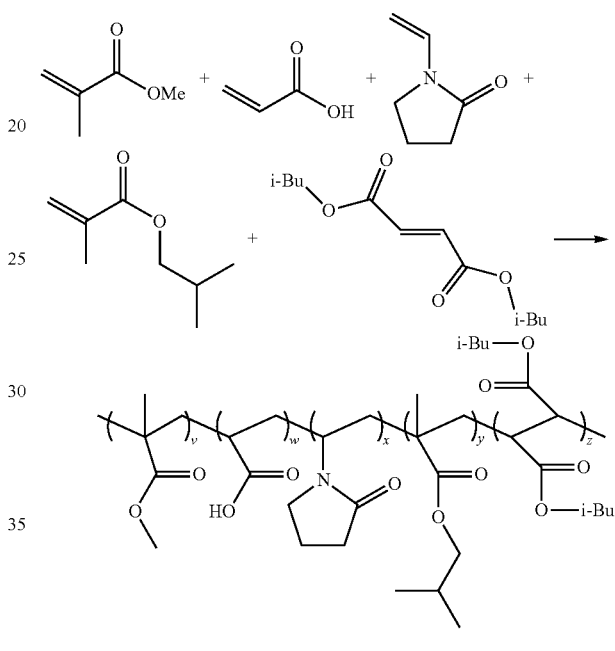

An autoclave reactor was loaded with t-butanol (238.0 g). A monomer solution of N-vinyl-2-pyrrolidone (42.68 g), acrylic acid (27.70 g), diisobutyl fumarate (43.85 g), methyl methacrylate (38.47 g) and isobutyl methacrylate (27.30 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 77° C. at t=5 hour and additional initiator was charged at t=6, 9 and 11 hour (0.72 g each). After the last initiator addition, stirring continued at 77° C. for 4 hours. After cooling, a viscous copolymer solution was discharged into a glass bottle.

This polymer was dried from solution, and the molecular weight was measured using gel permeation chromatography with poly(ethylene oxide) standards. The weight-average molecular weight ($M_w$) was found to be 116,300 Da, and the number-average molecular weight 24,500 Da.

The acid number was found to be 112.68 mg KOH/g or 2.0086 meq/g.

The polymer was found to be at least 50% (w/w) soluble in ethanol and at least 50% (w/w) in t-butanol. The glass transition temperature ($T_g$) was measured at 10° C./min and found to be 116° C.

Example 11: Synthesis of Poly(24.8% VP-24.8% AA-24.9% MMA-12.4% IBM-12.5% DIBF-0.6% tBAEMA)

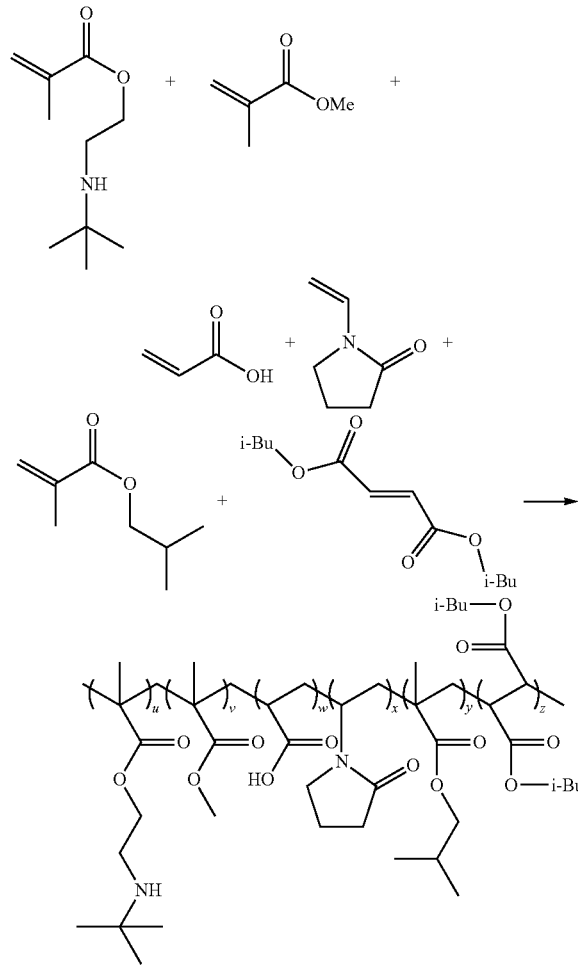

A 1-L glass reactor was loaded with t-butanol (276.19 g). A monomer solution of N-vinyl-2-pyrrolidone (47.00 g), acrylic acid (30.40 g), diisobutyl fumarate (48.20 g), methyl methacrylate (42.40 g), isobutyl methacrylate (30.00 g), and t-butylaminoethyl methacrylate (2.00 g) was prepared and charged into a syringe pump. Then, 20.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.51 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.51 g each). The reaction temperature then was raised to 75° C. at t=5 hour and additional initiator was charged at t=6, 9 and 11 hour (0.43 g each). After the last initiator addition, stirring continued at 75° C. for 4 hours. After cooling, a viscous copolymer solution was discharged into a glass bottle.

The polymer was found to be at least 50% (w/w) soluble in ethanol and at least 50% (w/w) in t-butanol.

Example 12: Synthesis of Poly(24.4% VP-24.4% AA-24.4% MMA-12.2% IBM-12.2% DIBF-2.4% tBAEMA)

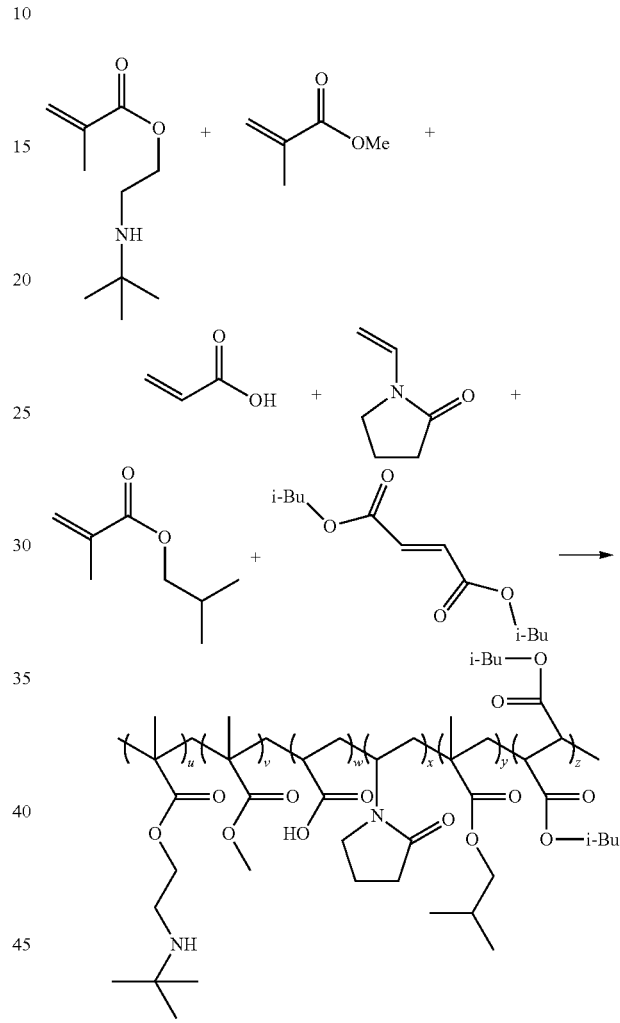

An autoclave reactor was loaded with t-butanol (211.0 g) and isopropanol (27.0 g). A monomer solution of N-vinyl-2-pyrrolidone (41.06 g), acrylic acid (26.66 g), diisobutyl fumarate (42.17 g), methyl methacrylate (37.01 g), isobutyl methacrylate (26.26 g) and t-butylaminoethyl methacrylate (6.84 g) was prepared and charged into a syringe pump. Then, 10.0% of the monomer solution was charged into the reactor. The mixture in the reactor was de-aerated and heated to 69° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

Example 13: Synthesis of Poly(24.6% VP-24.0% AA-24.7% MMA-12.3% IBM-12.3% DIBF-1.3% tBAEMA)

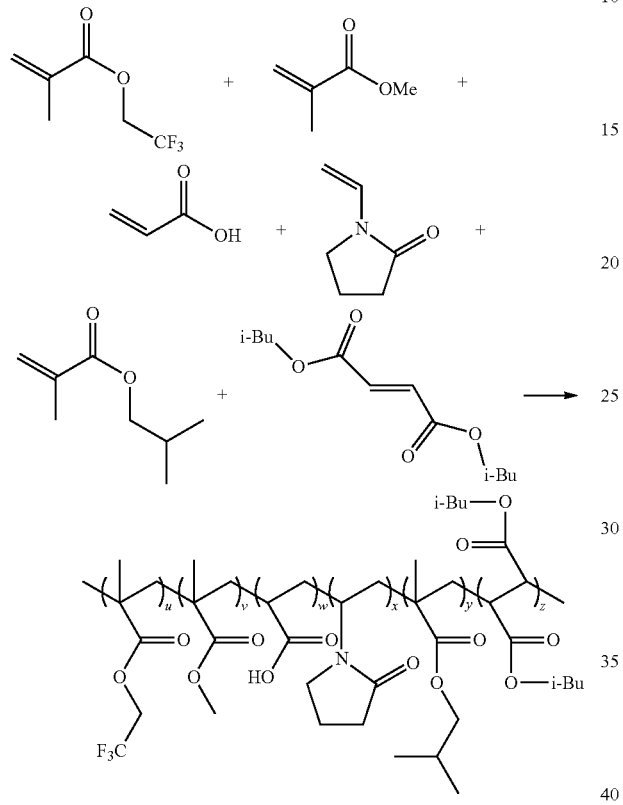

A 1-L jacketed glass reactor was loaded with t-butanol (2381.0 g). A monomer solution of N-vinyl-2-pyrrolidone (41.87 g), acrylic acid (27.19 g), diisobutyl fumarate (43.00 g), methyl methacrylate (37.74 g), isobutyl methacrylate (26.58 g) and 2,2,2-trifluoroethyl methacrylate (3.42 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

The polymer was found to be at least 50% (w/w) soluble in ethanol and at least 50% (w/w) in t-butanol. The glass transition temperature ($T_g$) was measured at 10° C./min and found to be 114° C.

Example 14: Synthesis of Poly(24.3% VP-24.3% AA-24.4% MMA-12.2% IBM-12.2% DIBF-2.7% TFEMA)

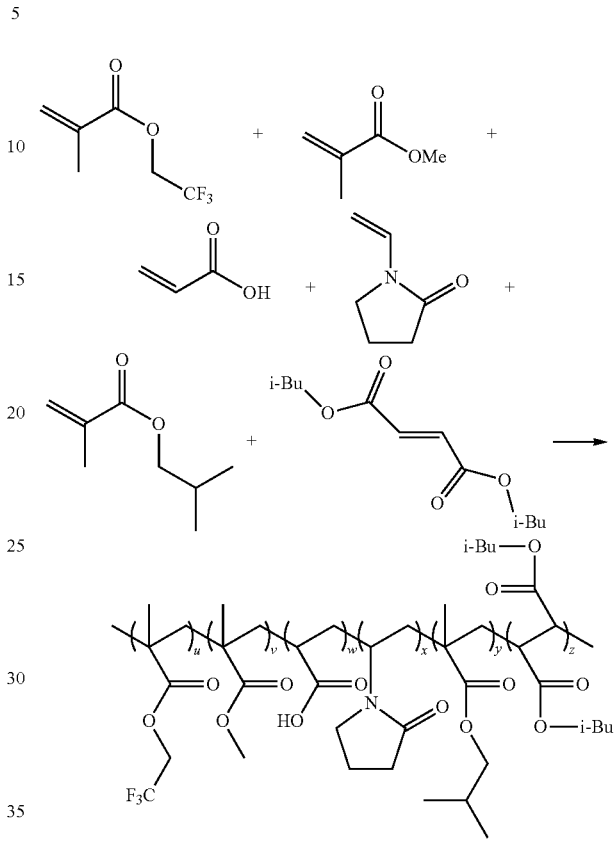

A 1-L jacketed glass reactor was loaded with t-butanol (238.0 g). A monomer solution of N-vinyl-2-pyrrolidone (41.06 g), acrylic acid (26.66 g), diisobutyl fumarate (42.17 g), methyl methacrylate (37.01 g), isobutyl methacrylate (26.26 g) and 2,2,2-trifluoroethyl methacrylate (6.84 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

The polymer was found to be at least 50% (w/w) soluble in ethanol and at least 50% (w/w) in t-butanol. The glass transition temperature ($T_g$) was measured at 10° C./min and found to be 116° C.

Example 15: Synthesis of Poly(23.9% VP-24.0% AA-23.9% MMA-12.0% IBM-12.0% DIBF-4.3% TFEMA)

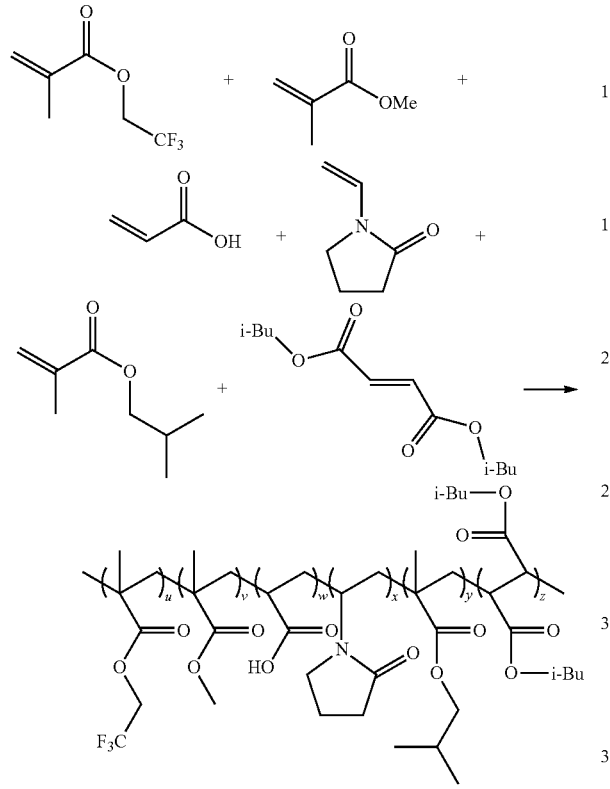

An autoclave reactor was loaded with t-butanol (238.0 g). A monomer solution of N-vinyl-2-pyrrolidone (40.10 g), acrylic acid (26.06 g), diisobutyl fumarate (41.28 g), methyl methacrylate (36.21 g), isobutyl methacrylate (25.72 g) and 2,2,2-trifluoroethyl methacrylate (10.80 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

The polymer was found to be at least 50% (w/w) soluble in ethanol and at least 50% (w/w) in t-butanol. The glass transition temperature ($T_g$) was measured at 10° C./min and found to be 113° C.

Example 16: Synthesis of Poly(24.7% VP-24.8% AA-24.8% MMA-12.4% IBM-12.4% DIBF-0.9% PEG/PPGMA)

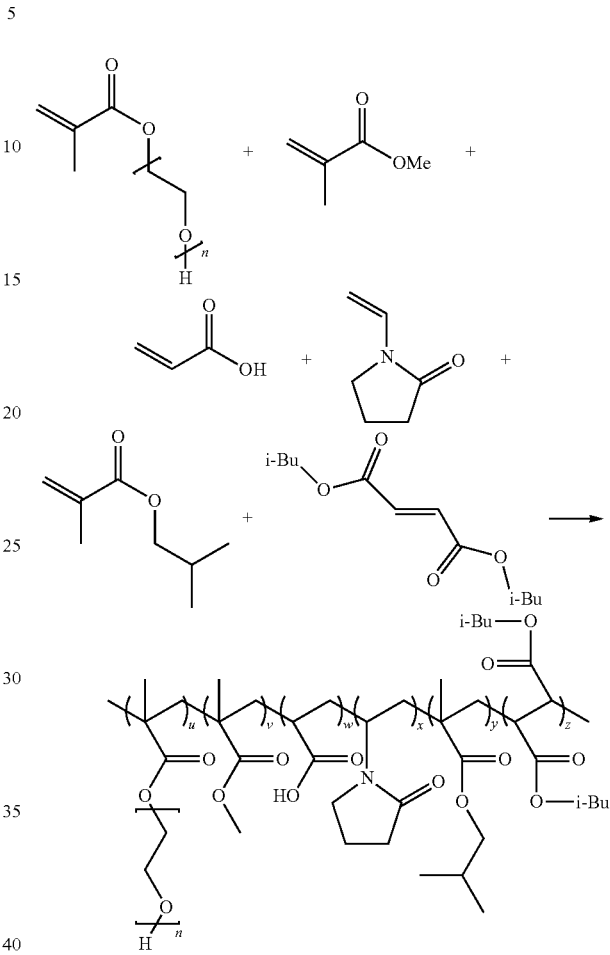

An autoclave reactor was loaded with t-butanol (238.0 g). A monomer solution of N-vinyl-2-pyrrolidone (41.06 g), acrylic acid (26.66 g), diisobutyl fumarate (42.17 g), methyl methacrylate (37.01 g), isobutyl methacrylate (26.26 g) and poly(ethylene glycol) methacrylate (average Mn=526) (6.84 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

The polymer was found to be at least 50% (w/w) soluble in ethanol and at least 50% (w/w) in t-butanol. The glass transition temperature ($T_g$) was measured at 10° C./min and found to be 110° C.

Example 17: Synthesis of Poly(24.6% VP-24.7% AA-24.7% MMA-12.3% IBM-12.4% DIBF-1.3% PEG/PPGMA)

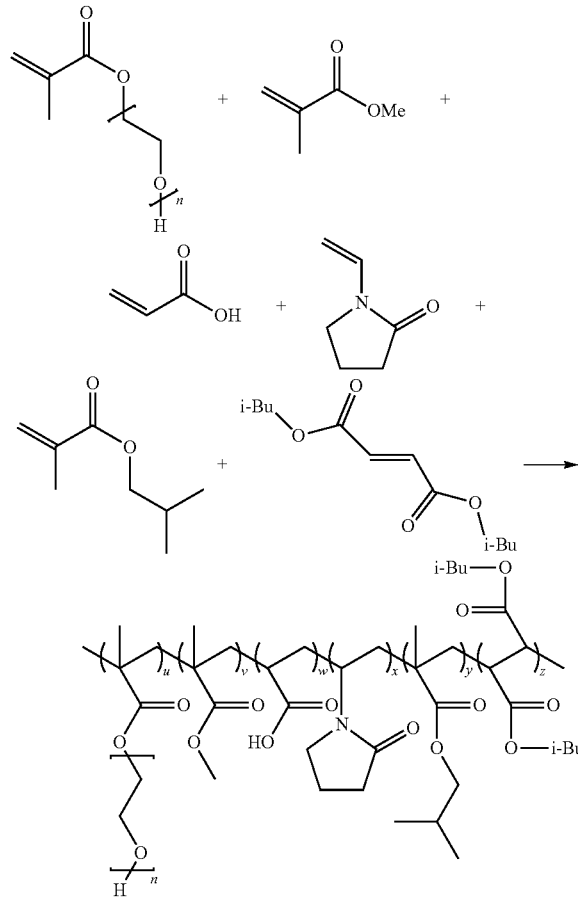

An autoclave reactor was loaded with t-butanol (238.0 g). A monomer solution of N-vinyl-2-pyrrolidone (41.06 g), acrylic acid (26.66 g), diisobutyl fumarate (42.17 g), methyl methacrylate (37.01 g), isobutyl methacrylate (26.26 g) and poly(ethylene glycol) methacrylate (Mn=360) (6.84 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

The polymer was found to be at least 50% (w/w) soluble in ethanol and at least 50% (w/w) in t-butanol.

Example 18: Synthesis of Poly(24.7% VP-24.7% AA-24.7% MMA-12.3% IBM-12.4% DIBF-1.2% PEG/PPGMA)

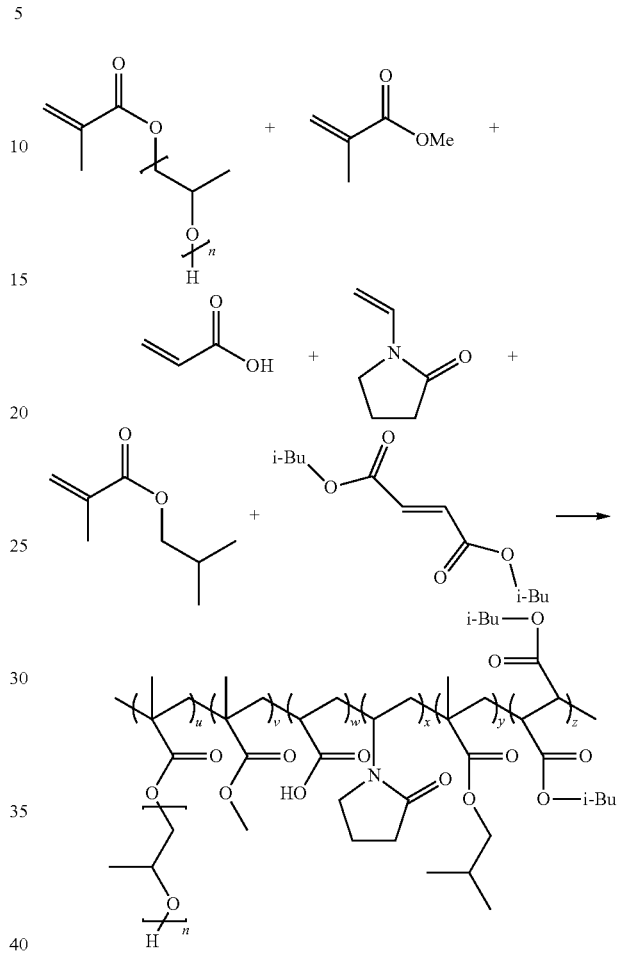

An autoclave reactor was loaded with t-butanol (238.0 g). A monomer solution of N-vinyl-2-pyrrolidone (41.06 g), acrylic acid (26.66 g), diisobutyl fumarate (42.17 g), methyl methacrylate (37.01 g), isobutyl methacrylate (26.26 g) and poly(propylene glycol) methacrylate (average Mn=375) (6.84 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

The polymer was found to be at least 50% (w/w) soluble in ethanol and at least 50% (w/w) in t-butanol. The glass transition temperature ($T_g$) was measured at 10° C./min and found to be 111° C.

Example 19: Synthesis of Poly(24.6% VP-24.7% AA-24.7% MMA-12.3% IBM-12.4% DIBF-1.3% PEG/PPGMA)

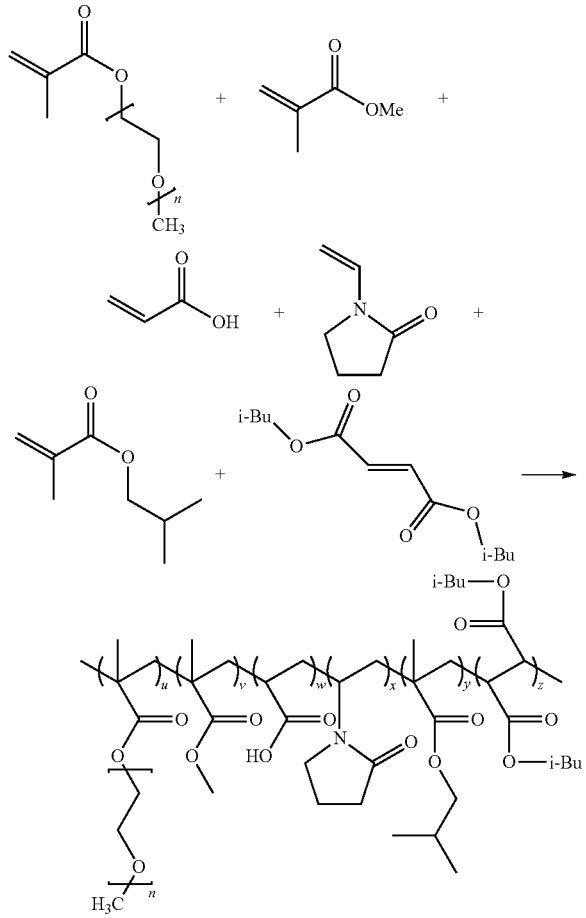

An autoclave reactor was loaded with t-butanol (238.0 g). A monomer solution of N-vinyl-2-pyrrolidone (41.06 g), acrylic acid (26.66 g), diisobutyl fumarate (42.17 g), methyl methacrylate (37.01 g), isobutyl methacrylate (26.26 g) and methoxy poly(ethylene glycol) methacrylate (average Mn=350) (6.84 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

The polymer was found to be at least 50% (w/w) soluble in ethanol and at least 50% (w/w) in t-butanol.

Example 20: Synthesis of Poly(25.0% VP-24.9% AA-25.0% MMA-12.5% IBM-12.5% DIBF-0.2% PEG/PPGMA)

A 1-L glass reactor was loaded with t-butanol (211.0 g) and isopropanol (27.0 g). A monomer solution of N-vinyl-2-pyrrolidone (42.68 g), acrylic acid (27.70 g), diisobutyl fumarate (43.85 g), methyl methacrylate (38.47 g), isobutyl methacrylate (27.30 g) and poly(ethylene glycol) diacrylate (average Mn=700) (1.80 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

The polymer was found to be at least 50% (w/w) soluble in ethanol and at least 50% (w/w) in t-butanol. The glass transition temperature ($T_g$) was measured at 10° C./min and found to be 112° C.

Example 21: Synthesis of Poly(25.0% VP-24.9% AA-25.0% MMA-12.5% IBM-12.5% DIBF-0.2% PEG/PPGMA)

A 1-L glass reactor was loaded with t-butanol (211.0 g) and isopropanol (27.0 g). A monomer solution of N-vinyl-2-pyrrolidone (42.68 g), acrylic acid (27.70 g), diisobutyl fumarate (43.85 g), methyl methacrylate (38.47 g), isobutyl methacrylate (27.30 g) and trimethylolpropane ethoxylate triacrylate (average Mn=692) (1.80 g) was prepared and charged into a syringe pump. Then, 5.0% of the monomer solution was charged into the reactor. The mixture in the reactor was de-aerated and heated to 70° C. under nitrogen with mechanical stirring at 200 rpm. At t=0, t-butyl peroxypivalate initiator (Trigonox® 25-C75, Akzo Nobel) (0.72 g) was charged into the reactor to initiate the polymerization. Then, the remaining monomer solution in the syringe pump was emptied into the reactor at a constant rate over the next 4 hours. Additional shots of the initiator were added at t=1, 2, 3, 4 hour (0.72 g each). The reaction temperature then was raised to 76° C. at t=5 hour and additional initiator was charged at t=6, 9 and 11 hour (0.72 g each). After the last initiator addition, stirring continued at 76° C. for 4 hours. After cooling, a viscous copolymer solution was discharged into a glass bottle.

The polymer was found to be at least 50% (w/w) soluble in ethanol and at least 50% (w/w) in t-butanol. The glass transition temperature ($T_g$) was measured at 10° C./min and found to be 116° C.

Example 22: Synthesis of Poly(25.0% VP-25.0% AA-25.0% MMA-12.5% IBM-12.5% DBM)

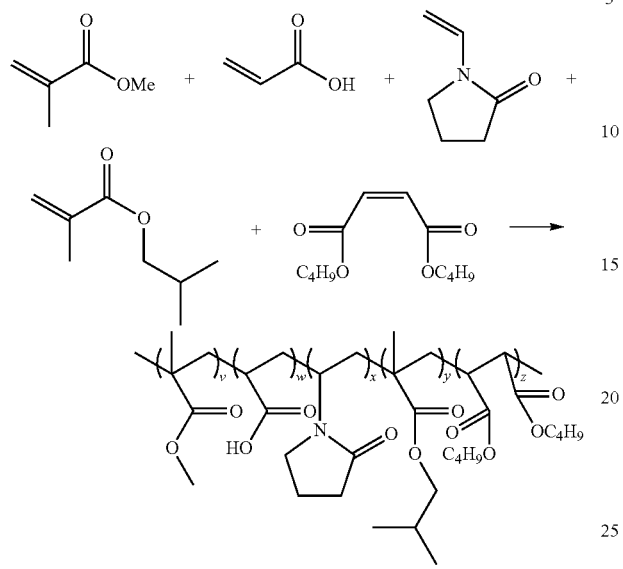

A 1-L jacketed glass reactor was loaded with t-butanol (173.14 g). A monomer solution of N-vinyl-2-pyrrolidone (53.28 g), acrylic acid (34.56 g), di-n-butyl maleate (54.72 g), methyl methacrylate (48.00 g) and isobutyl methacrylate (34.08 g) was prepared and charged into a syringe pump. Then, 33.3% of the monomer solution was charged into the reactor. The mixture in the reactor was de-aerated and heated to 68° C. under nitrogen with mechanical stirring at 200 rpm. At t=0, t-butyl peroxypivalate initiator (Trigonox® 25-C75, Akzo Nobel) (0.24 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.24 g each). The reaction temperature then was raised to 75° C. at t=4 hour and additional initiator was charged at t=5, 8 and 10 hour (0.64 g each). After the last initiator addition, stirring continued at 75° C. for 4 hours. After cooling, a viscous copolymer solution was discharged into a glass bottle.

The polymer was found to be at least 50% (w/w) soluble in ethanol and at least 50% (w/w) in t-butanol. The glass transition temperature ($T_g$) was measured at 10° C./min and found to be 83° C.

Example 23: Synthesis of Poly(21% VP-24.3% AA-29.1% MMA-12.3% IBM-10.2% DBM-3.1% tBAEMA)

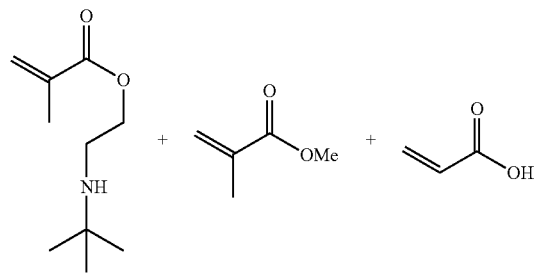

Example (continued)

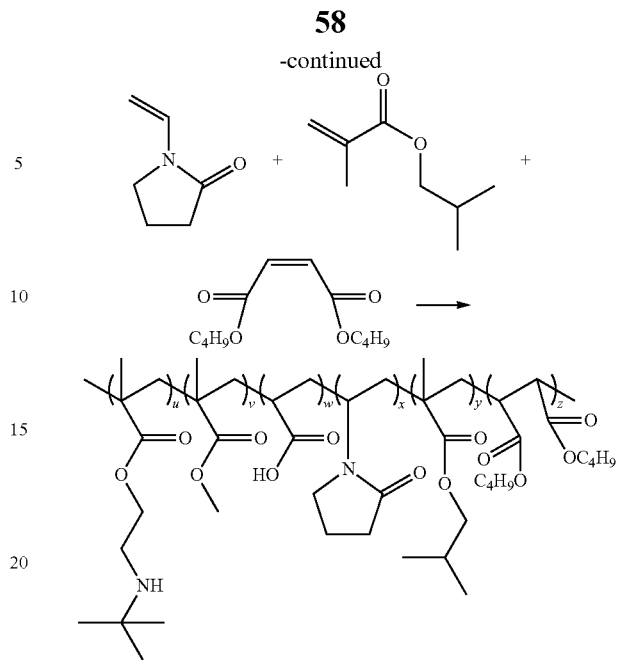

A 1-L jacketed glass reactor was loaded with t-butanol (84.70 g). A monomer solution of N-vinyl-2-pyrrolidone (40.00 g), acrylic acid (30.00 g), di-n-butyl maleate (40.00 g), methyl methacrylate (50.00 g) and isobutyl methacrylate (30.00 g) and t-butylaminoethyl methacrylate (10.00 g) was prepared and charged into a syringe pump. Then, 33.3% of the monomer solution was charged into the reactor. The mixture in the reactor was de-aerated and heated to 68° C. under nitrogen with mechanical stirring at 200 rpm. At t=0, t-butyl peroxypivalate initiator (Trigonox® 25-C75, Akzo Nobel) (0.21 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.21 g each). The reaction temperature then was raised to 75° C. at t=4 hour and additional initiator was charged at t=5, 8 and 10 hour (0.57 g each). After the last initiator addition, stirring continued at 75° C. for 4 hours. After cooling, a viscous copolymer solution was discharged into a glass bottle.

Example 24: Synthesis of Poly(16.0% VP-27.9% AA-41.4% MMA-4.1% HPMA-8.7% DOM-1.9% tBAEMA)

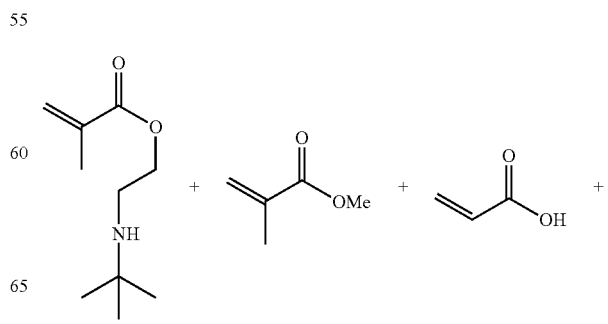

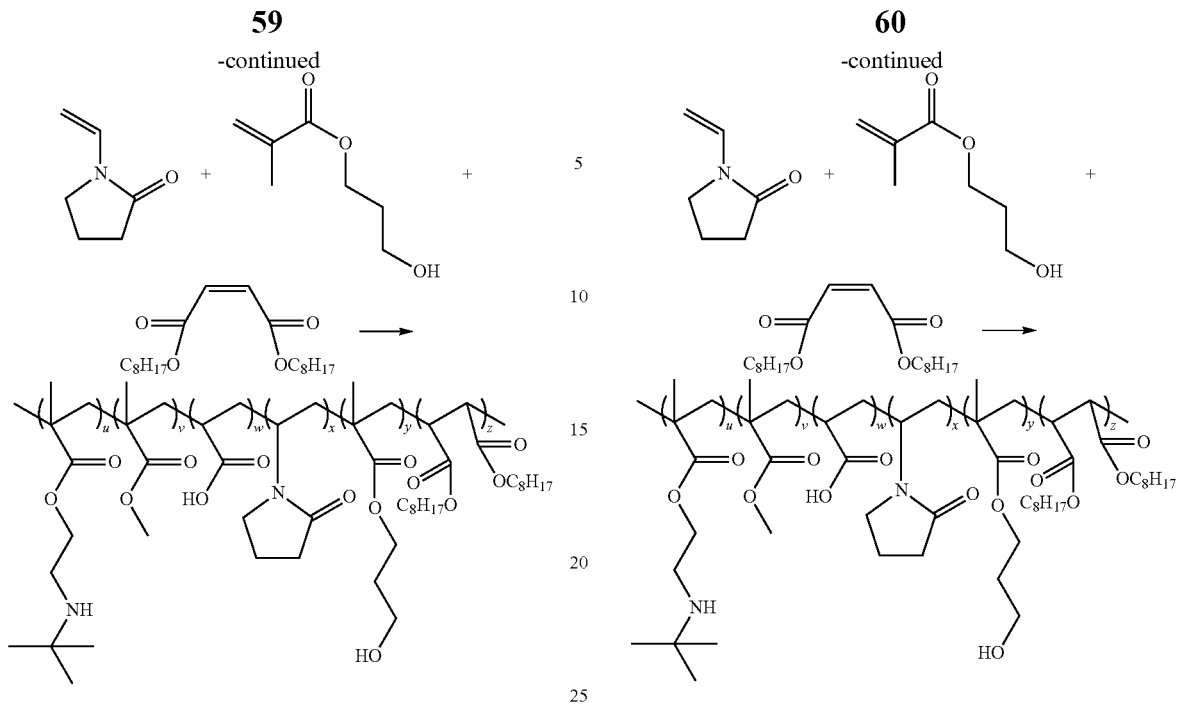

An autoclave reactor was loaded with t-butanol (249.00 g). A monomer solution of N-vinyl-2-pyrrolidone (27.00 g), acrylic acid (30.60 g), di-octyl maleate (45.00 g), methyl methacrylate (63.00 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.32 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.32 g each). The reaction temperature then was raised to 91° C. at t=4 hour and additional initiator was charged at t=5, 8 and 10 hour (0.75 g each). After the last initiator addition, stirring continued at 91° C. for 4 hours. Then, DI water (30.00 g) was added into the reactor and stirred for 30 min. After cooling, a viscous copolymer solution was discharged into a glass bottle.

The glass transition temperature ($T_g$) was measured at 10° C./min and found to be 127° C.

Example 25: Synthesis of Poly(19.8% VP-25.9% AA-43.9% MMA-3.8% HPMA-4.8% DOM-1.8% tBAEMA)

An autoclave reactor was loaded with t-butanol (242.00 g). A monomer solution of N-vinyl-2-pyrrolidone (36.00 g), acrylic acid (30.60 g), di-octyl maleate (27.00 g), methyl methacrylate (72.00 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.28 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.28 g each). The reaction temperature then was raised to 91° C. at t=4 hour and additional initiator was charged at t=5, 8 and 10 hour (0.75 g each). After the last initiator addition, stirring continued at 91° C. for 4 hours. Then, DI water (30.00 g) was added into the reactor and stirred for 30 min. After cooling, a viscous copolymer solution was discharged into a glass bottle.

The glass transition temperature ($T_g$) was measured at 10° C./min and found to be 143° C.

Example 26: Synthesis of Poly(20.6% VP-27.0% AA-39.9% MMA-4.0% HPMA-6.7% DOM-1.9% tBAEMA)

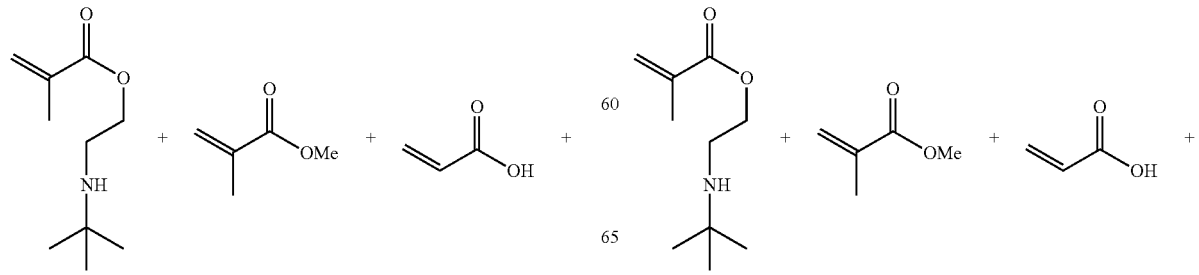

-continued

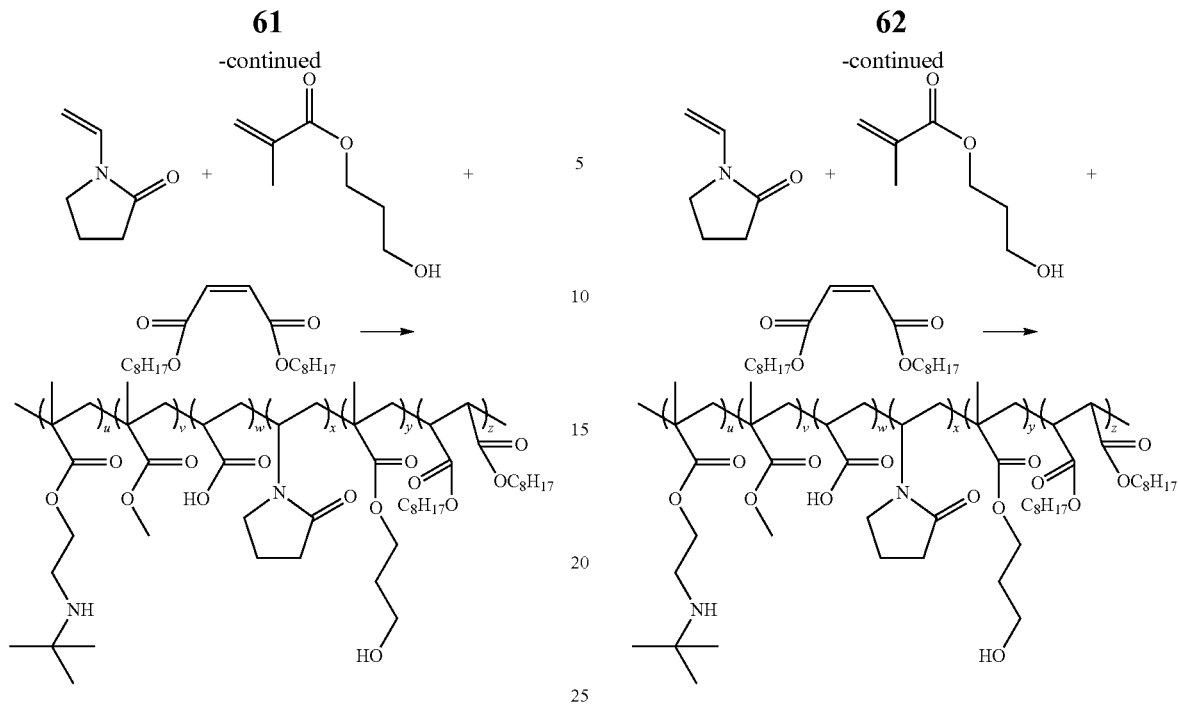

An autoclave reactor was loaded with t-butanol (242.00 g). A monomer solution of N-vinyl-2-pyrrolidone (36.00 g), acrylic acid (30.60 g), di-octyl maleate (36.00 g), methyl methacrylate (63.00 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.32 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.32 g each). The reaction temperature then was raised to 91° C. at t=4 hour and additional initiator was charged at t=5, 8 and 10 hour (0.75 g each). After the last initiator addition, stirring continued at 91° C. for 4 hours. Then, DI water (30.00 g) was added into the reactor and stirred for 30 min. After cooling, a viscous copolymer solution was discharged into a glass bottle.

The glass transition temperature ($T_g$) was measured at 10° C./min and found to be 134° C.

Example 27: Synthesis of Poly(23.7% VP-27.1% AA-36.6% MMA-4.0% HPMA-6.7% DOM-1.9% tBAEMA)

An autoclave reactor was loaded with t-butanol (249.00 g). A monomer solution of N-vinyl-2-pyrrolidone (41.40 g), acrylic acid (30.60 g), di-octyl maleate (36.00 g), methyl methacrylate (57.60 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.32 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.32 g each). The reaction temperature then was raised to 91° C. at t=4 hour and additional initiator was charged at t=5, 8 and 10 hour (0.75 g each). After the last initiator addition, stirring continued at 91° C. for 4 hours. Then, DI water (30.00 g) and sodium metabisulfite (0.24 g) were added into the reactor and stirred for 30 min. After cooling, a viscous copolymer solution was discharged into a glass bottle.

The glass transition temperature ($T_g$) was measured at 10° C./min and found to be 138° C.

Example 28: Synthesis of Poly(31.2% VP-27.3% AA-28.9% MMA-4.0% HPMA-6.8% DOM-1.9% tBAEMA)

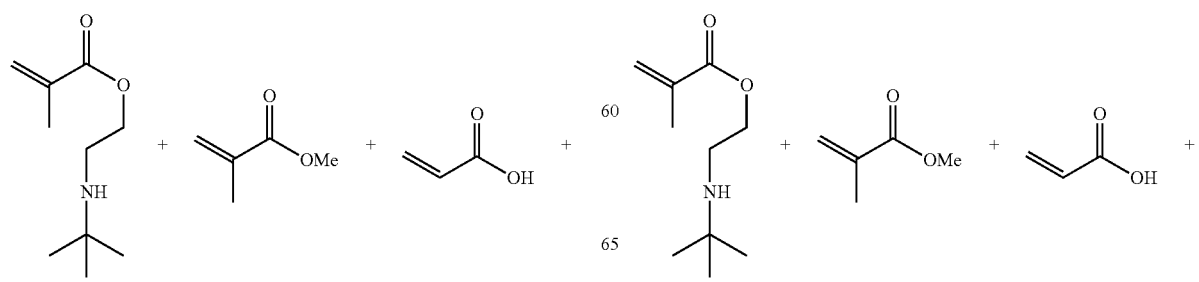

-continued

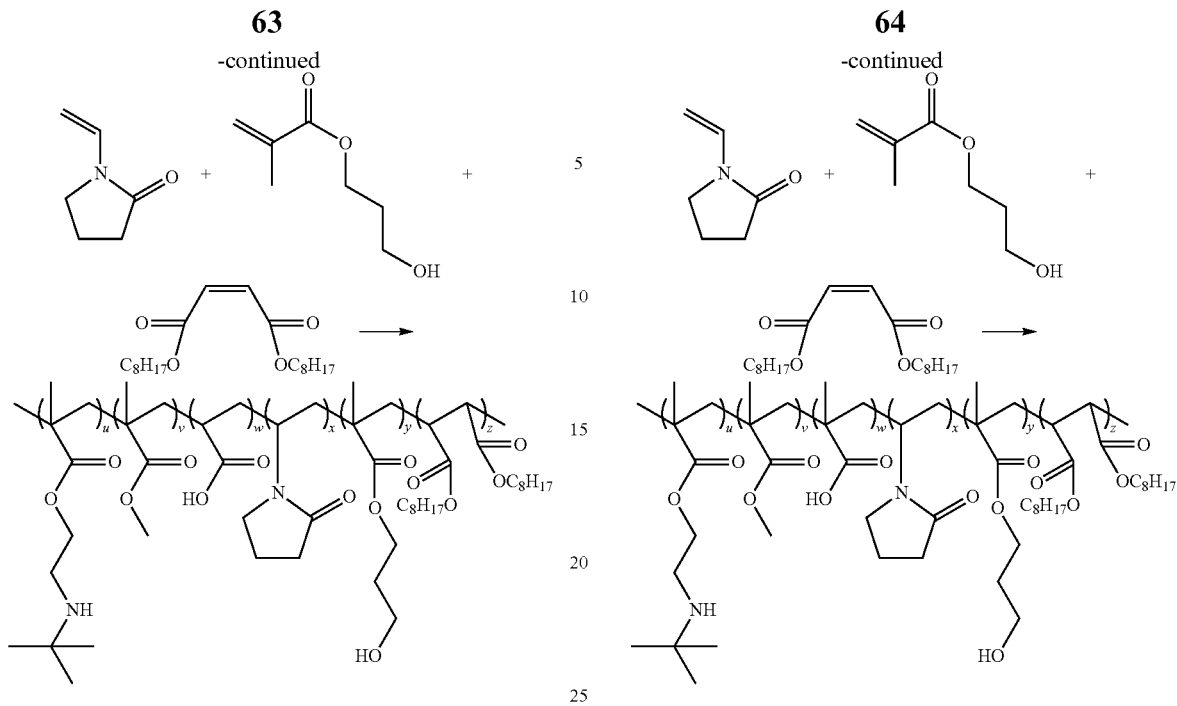

An autoclave reactor was loaded with t-butanol (249.00 g). A monomer solution of N-vinyl-2-pyrrolidone (54.00 g), acrylic acid (30.60 g), di-octyl maleate (36.00 g), methyl methacrylate (45.00 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.32 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.32 g each). The reaction temperature then was raised to 91° C. at t=4 hour and additional initiator was charged at t=5, 8 and 10 hour (0.75 g each). After the last initiator addition, stirring continued at 91° C. for 4 hours. Then, DI water (30.00 g) and sodium metabisulfite (0.24 g) were added into the reactor and stirred for 30 min. After cooling, a viscous copolymer solution was discharged into a glass bottle.

Example 29: Synthesis of Poly(21.5% VP-24.9% MAA-40.5% MMA-4.1% HPMA-7.0% DOM-1.9% tBAEMA)

An autoclave reactor was loaded with t-butanol (242.00 g). A monomer solution of N-vinyl-2-pyrrolidone (36.00 g), methacrylic acid (32.40 g), di-octyl maleate (36.00 g), methyl methacrylate (61.20 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.28 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.28 g each). The reaction temperature then was raised to 91° C. at t=4 hour and additional initiator was charged at t=5, 8 and 10 hour (0.75 g each). After the last initiator addition, stirring continued at 91° C. for 4 hours. Then, DI water (30.00 g) was added into the reactor and stirred for 30 min. After cooling, a viscous copolymer solution was discharged into a glass bottle.

The glass transition temperature ($T_g$) was measured at 10° C./min and found to be 179° C.

Example 30: Synthesis of Poly(25.9% VP-24.1% MAA-39.1% MMA-4.0% HPMA-5.1% DOM-1.9% tBAEMA)

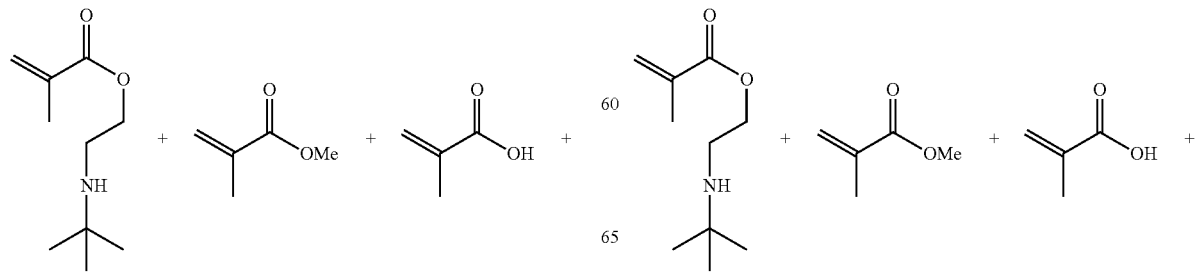

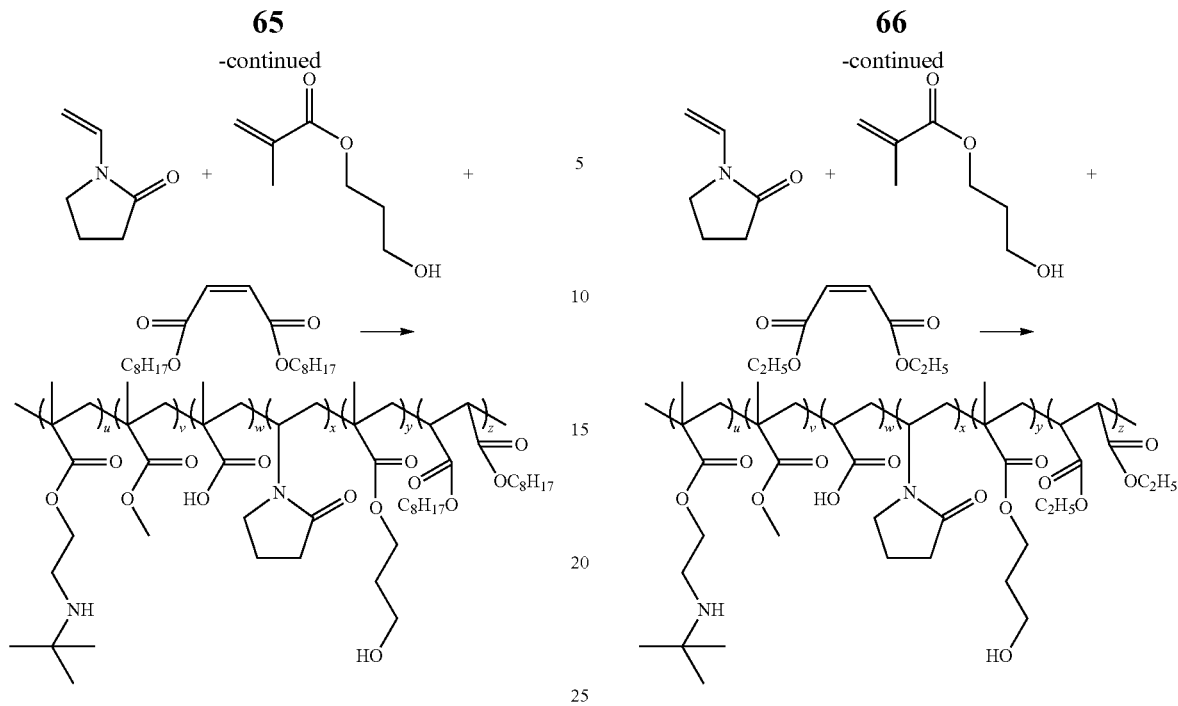

An autoclave reactor was loaded with t-butanol (242.00 g). A monomer solution of N-vinyl-2-pyrrolidone (45.00 g), methacrylic acid (32.40 g), di-octyl maleate (27.00 g), methyl methacrylate (61.20 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.28 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.28 g each). The reaction temperature then was raised to 91° C. at t=4 hour and additional initiator was charged at t=5, 8 and 10 hour (0.75 g each). After the last initiator addition, stirring continued at 91° C. for 4 hours. Then, DI water (30.00 g) was added into the reactor and stirred for 30 min. After cooling, a viscous copolymer solution was discharged into a glass bottle.

The glass transition temperature ($T_g$) was measured at 10° C./min and found to be 182° C.

An autoclave reactor was loaded with t-butanol (165.00 g). A monomer solution of N-vinyl-2-pyrrolidone (20.00 g), acrylic acid (34.00 g), di-ethyl maleate (30.00 g), methyl methacrylate (100.00 g), hydroxypropyl methacrylate (10.00 g) and t-butylaminoethyl methacrylate (6.00 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.28 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.28 g each). The reaction temperature then was raised to 91° C. at t=4 hour and additional initiator was charged at t=5, 8 and 10 hour (0.75 g each). After the last initiator addition, stirring continued at 91° C. for 4 hours. After cooling, a viscous copolymer solution was discharged into a glass bottle.

The glass transition temperature ($T_g$) was measured at 10° C./min and found to be 92° C.

Example 31: Synthesis of Poly(9.3% VP-24.5% AA-51.8% MMA-3.6% HPMA-9.0% DEM-1.7% tBAEMA)

Example 32: Synthesis of Poly(16.2% VP-25.0% AA-42.3% MMA-3.7% HPMA-11.1% DEM-1.7% tBAEMA)

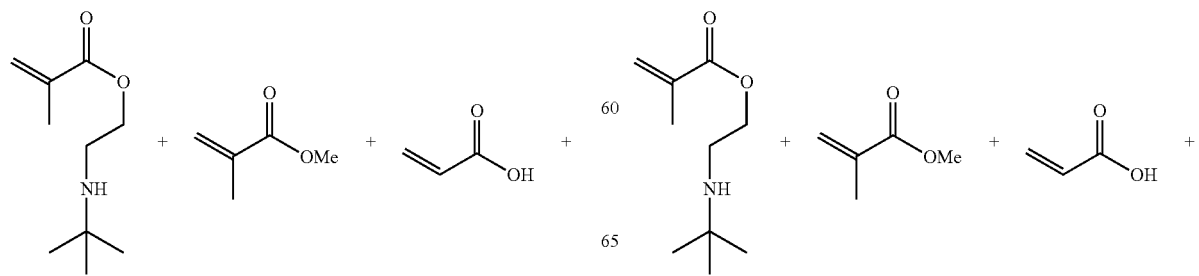

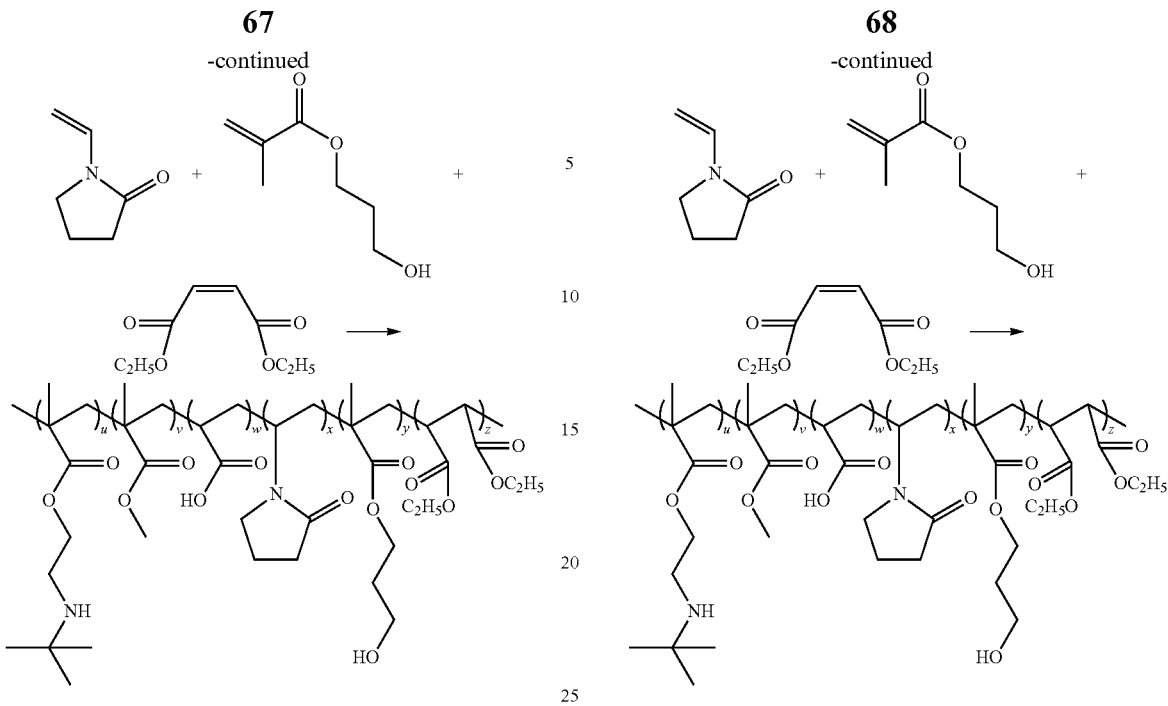

An autoclave reactor was loaded with t-butanol (148.50 g). A monomer solution of N-vinyl-2-pyrrolidone (30.60 g), acrylic acid (30.60 g), di-ethyl maleate (32.40 g), methyl methacrylate (72.00 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.28 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.28 g each). The reaction temperature then was raised to 91° C. at t=4 hour and additional initiator was charged at t=5, 8 and 10 hour (0.75 g each). After the last initiator addition, stirring continued at 91° C. for 4 hours. Then, DI water (100.00 g) was added into the reactor and stirred for 30 min. After cooling, a viscous copolymer solution was discharged into a glass bottle.

An autoclave reactor was loaded with t-butanol (148.50 g). A monomer solution of N-vinyl-2-pyrrolidone (34.20 g), acrylic acid (30.60 g), di-ethyl maleate (28.80 g), methyl methacrylate (72.00 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.28 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.28 g each). The reaction temperature then was raised to 91° C. at t=4 hour and additional initiator was charged at t=5, 8 and 10 hour (0.75 g each). After the last initiator addition, stirring continued at 91° C. for 4 hours. Then, DI water (100.00 g) was added into the reactor and stirred for 30 min. After cooling, a viscous copolymer solution was discharged into a glass bottle.

Example 33: Synthesis of Poly(18.0% VP-24.8% AA-42.0% MMA-3.6% HPMA-9.8% DEM-1.7% tBAEMA)

Example 34: Synthesis of Poly(16.7% VP-25.7% AA-43.5% MMA-3.8% HPMA-8.6% DIBF-1.8% tBAEMA)

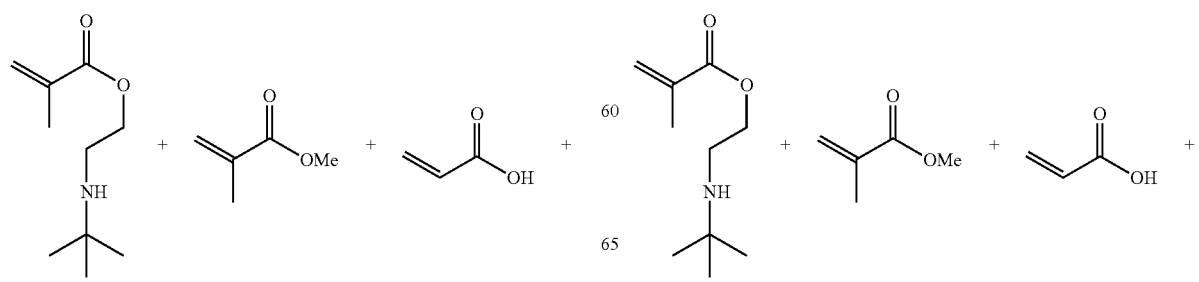

-continued

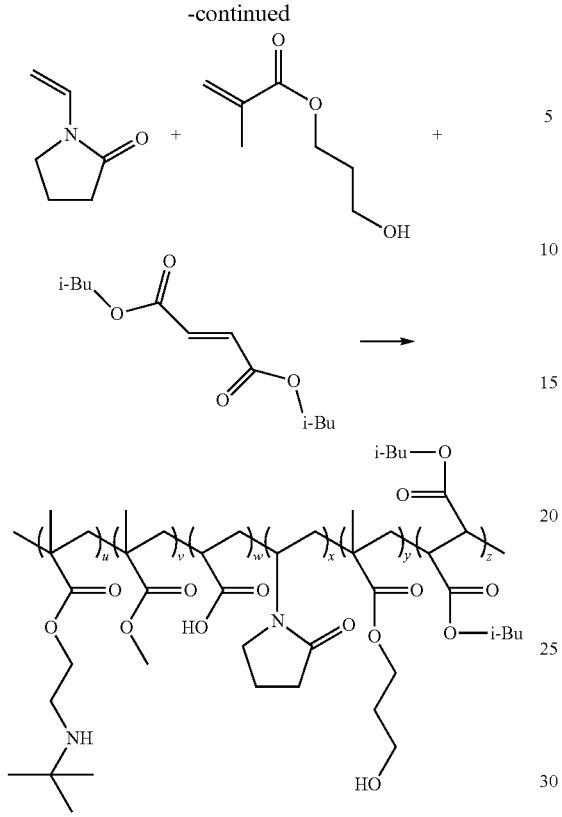

An autoclave reactor was loaded with t-butanol (148.50 g). A monomer solution of N-vinyl-2-pyrrolidone (30.60 g), acrylic acid (30.60 g), di-isobutyl fumarate (32.40 g), methyl methacrylate (72.00 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.28 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.28 g each). The reaction temperature then was raised to 91° C. at t=4 hour and additional initiator was charged at t=5, 8 and 10 hour (0.75 g each). After the last initiator addition, stirring continued at 91° C. for 4 hours. Then, ethanol (45.00 g) and DI water (45.00 g) were added into the reactor and stirred for 30 min. After cooling, a viscous copolymer solution was discharged into a glass bottle.

The polymer was found to be at least 50% (w/w) soluble in ethanol.

Example 35: Synthesis of Poly(18.1% VP-26.4% AA-39.1% MMA-3.9% HPMA-10.8% DEM-1.8% tBAEMA)

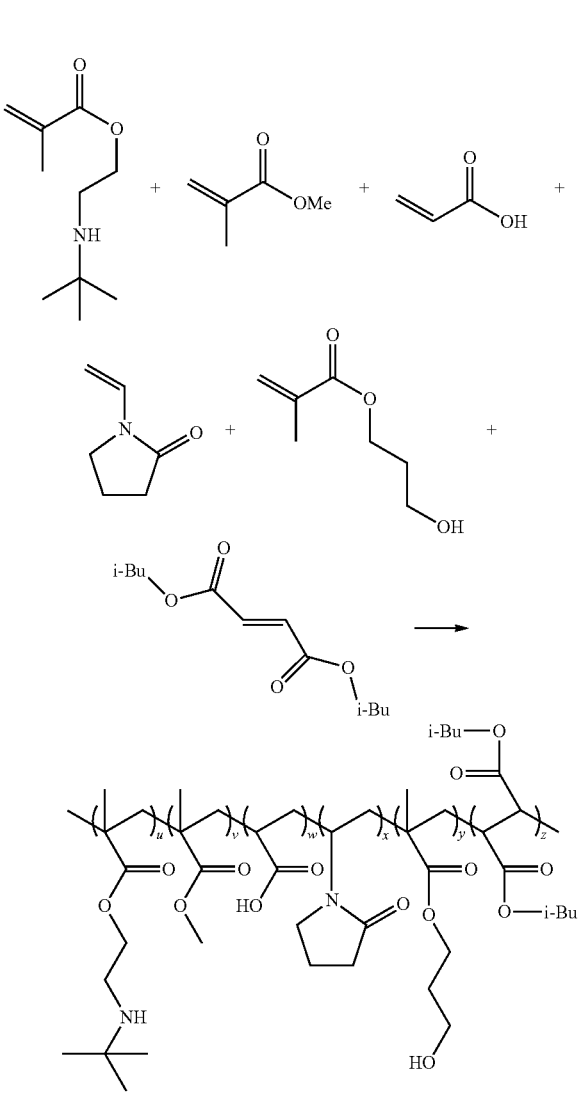

An autoclave reactor was loaded with t-butanol (148.50 g). A monomer solution of N-vinyl-2-pyrrolidone (32.40 g), acrylic acid (30.60 g), di-isobutyl fumarate (39.60 g), methyl methacrylate (63.00 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.28 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.28 g each). The reaction temperature then was raised to 91° C. at t=4 hour and additional initiator was charged at t=5, 8 and 10 hour (0.75 g each). After the last initiator addition, stirring continued at 91° C. for 4 hours. Then, ethanol (45.00 g) and DI water (45.00 g) were added into the reactor and stirred for 30 min. After cooling, a viscous copolymer solution was discharged into a glass bottle.

The glass transition temperature ($T_g$) was measured at 10° C./min and found to be 118° C.

Example 36: Synthesis of Poly(21.3% VP-27.5% MAA-32.4% IBM-4.6% HPMA-12.1% DIBF-2.1% tBAEMA)

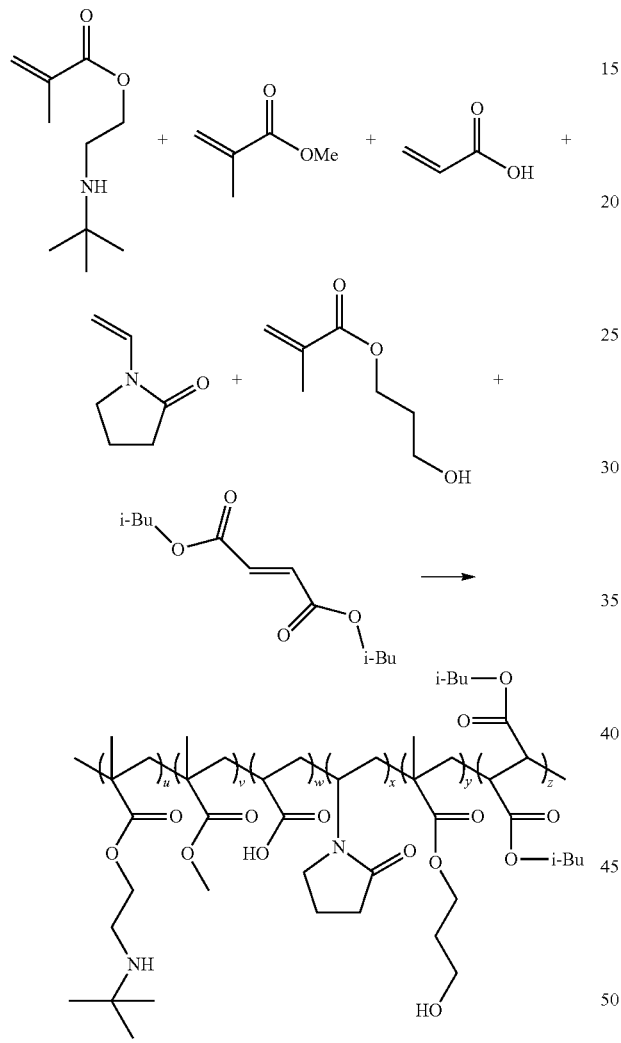

An autoclave reactor was loaded with t-butanol (148.50 g). A monomer solution of N-vinyl-2-pyrrolidone (32.40 g), methacrylic acid (32.40 g), di-isobutyl fumarate (37.80 g), isobutyl methacrylate (63.00 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.28 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.28 g each). The reaction temperature then was raised to 91° C. at t=4 hour and additional initiator was charged at t=5, 8 and 10 hour (0.75 g each). After the last initiator addition, stirring continued at 91° C. for 4 hours. Then, ethanol (45.00 g) and DI water (45.00 g) were added into the reactor and stirred for 30 min. After cooling, a viscous copolymer solution was discharged into a glass bottle.

The glass transition temperature ($T_g$) was measured at 10° C./min and found to be 141° C.

Example 37: Synthesis of Poly(21.9% VP-29.8% MAA-31.6% IBMA-4.5% HPMA-10.1% DIBF-2.1% tBAEMA)

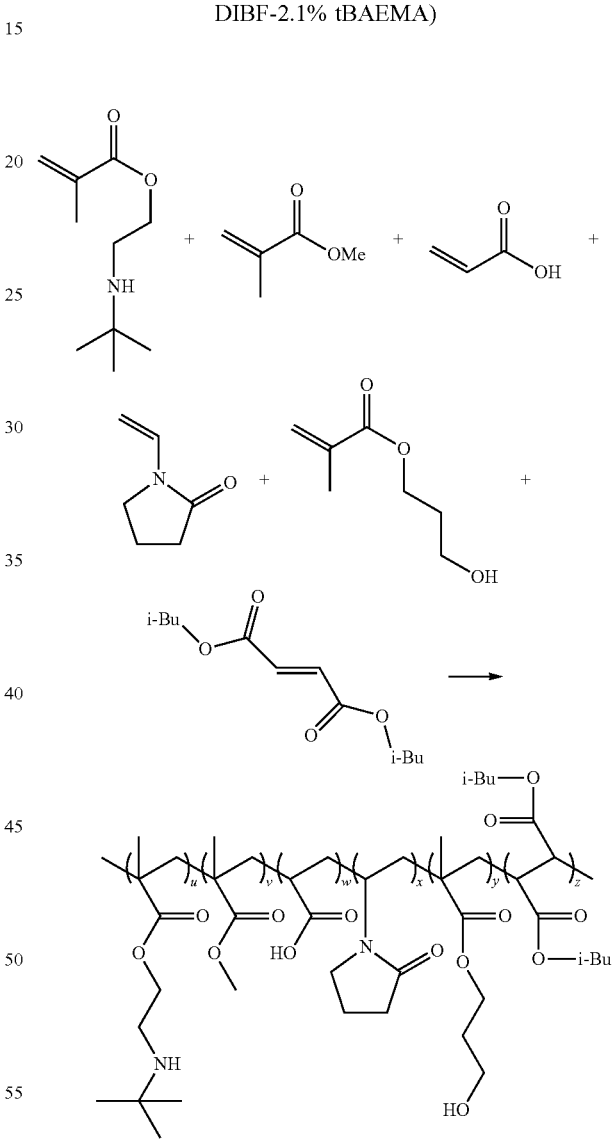

An autoclave reactor was loaded with t-butanol (148.50 g). A monomer solution of N-vinyl-2-pyrrolidone (34.20 g), methacrylic acid (36.00 g), di-isobutyl fumarate (32.40 g), isobutyl methacrylate (63.00 g), hydroxypropyl methacrylate (9.00 g) and t-butylaminoethyl methacrylate (5.40 g) was prepared and charged into a syringe pump. Then, 25.0% of the monomer solution was charged into the reactor. The mixture in the reactor was de-aerated and heated to 85° C. under nitrogen with mechanical stirring at 200 rpm. At t=0, t-amyl peroxy-2-ethylhexanoate initiator (Trigonox® 121, Akzo Nobel) (0.28 g) was charged into the reactor to initiate the polymerization. Then, the remaining monomer solution in the syringe pump was emptied into the reactor at a constant rate over the next 3 hours. Additional shots of the initiator were added at t=1, 2, 3 hour (0.28 g each). The reaction temperature then was raised to 91° C. at t=4 hour and additional initiator was charged at t=5, 8 and 10 hour (0.75 g each). After the last initiator addition, stirring continued at 91° C. for 4 hours. Then, ethanol (45.00 g) and DI water (45.00 g) were added into the reactor and stirred for 30 min. After cooling, a viscous copolymer solution was discharged into a glass bottle.

The glass transition temperature ($T_g$) was measured at 10° C./min and found to be 155° C.

Example 38: Hair Spray Formulations

The polymer of Example 8 was dried to yield a powder, which then was formulated at 5% addition level into 7 hair sprays. These formulas can be characterized in a number of different ways:

- having hydrocarbon, dimethyl ether, or hydrofluorocarbon propellant (A-D)
- non-aerosol (not containing propellant, E-G),
- 55% (w/w) high volatile organic carbon (VOC) aerosol (A, B)
- high VOC aerosol (C, D)
- 55% VOC non-aerosol (E)
- high VOC non-aerosol (F), and
- water-based, non-aerosol (G).

The hair sprays exhibited room temperature compatibility; they did not phase-separate, coagulate, nor settle. The aerosol formulas (A-D) had a cloud point less than −30° C., and the non-aerosol formulas had a Brookfield viscosity of 21.8 cP or less when measured at 25° C. using UL Adapter and at 12 rpm. Formula A, which contained almost 39% water, passed the 96-hour closed-cell, gavanic corrosion screening test, as no corrosion was observed after 96 hours. The gavanic corrosion test followed the method disclosed in the reference by Maria E. Boulden, "Corrosion Inhibitors for Water based Aerosol Formulations," *Spray Technology and Marketing*, April 1993.

TABLE 1

Hair spray formulas of Example 38

| ingredient | A | B | C | D | E | F | G |
|---|---|---|---|---|---|---|---|
| water | 38.60 | 0.00 | 0.00 | 0.00 | 38.60 | 0.00 | 94.02 |
| ethanol 200 | 20.00 | 55.00 | 59.10 | 52.10 | 55.00 | 94.10 | |
| aminomethyl propanol | 0.90 | 0.90 | 0.90 | 0.90 | 0.90 | 0.90 | 0.98 |
| polymer of Example 8 | 5.00 | 5.00 | 5.00 | 5.00 | 5.00 | 5.00 | 5.00 |
| mono ethanolamine/mono isopropylamine borate | 0.25 | | | | 0.25 | | |
| ammonium hydroxide (28% aq) | 0.25 | | | | 0.25 | | |
| dimethyl ether | 35.00 | | | | | | |
| hydrocarbon (A-46) | | | 35.00 | 42.00 | | | |
| hydrofluorocarbon 152a† | | 39.10 | | | | | |
| total: | 100.00 | 100.00 | 100.00 | 100.00 | 100.00 | 100.00 | 100.00 |
| room temp compatibility | yes | yes | yes | yes | yes | yes | yes |
| cloud point | <−30 C. | <−30 C. | <−30 C. | <−30 C. | | | |
| Brookfield viscosity, ULA 25 C., 12 rpm | | | | | | 21.8 | 6.4 | 10.3 |
| 96 hour Closed Cell Galvanic Corrosion Screening | None obs. | | | | | | |

†Hydrocarbon 152a is not considered to be a VOC propellant according to the EPA definition of VOC, 40 CFR 51 as a January 2009.

Example 39: Hair Spray Formulations

Polymers of the invention were dried to yield a powder (except where noted), which then was formulated at 5% addition level into 5 hair sprays (Table 2). The formula solutions were clear, and dried to clear films on glass. Additionally, a droplet of water placed on the dried film remained clear, and the film maintained clarity after drying. Solution viscosities ranged from about 17-25 cP when measured using a Brookfield ULA viscometer operating at 12 rpm. A high-humidity, curl-retention evaluation found that 92-96% of the hair curl was retained after 24 hours.

TABLE 2

Fifty-five percent ethanol hair spray formulas of Example 39

| ingredient | A | B | C | D | E |
|---|---|---|---|---|---|
| water | 39.11 | 39.12 | 39.11 | 39.06 | 39.08 |
| ethanol 200 | 55.00 | 55.00 | 55.00 | 55.00 | 55.00 |
| aminomethyl propanol | 0.89 | 0.88 | 0.89 | 0.94 | 0.92 |
| polymer of Example 7 (solid) | 5.00 | | | | |
| polymer of Example 15 (solid) | | 5.00 | | | |
| polymer of Example 18 (solid) | | | 5.00 | | |
| polymer of Example 11 (51.2% solids in t-BuOH) | | | | 5.00 | |
| polymer of Example 21 (solid) | | | | | 5.00 |
| total: | 100.00 | 100.00 | 100.00 | 100.00 | 100.00 |
| appearance | clear soln | clear soln | clear soln | clear soln | clear soln |

TABLE 2-continued

Fifty-five percent ethanol hair spray formulas of Example 39

| ingredient | formula (w/w) | | | | |
|---|---|---|---|---|---|
| | A | B | C | D | E |
| film on glass | clear | clear | clear | clear | clear |
| film on glass + water drop | clear | clear | clear | clear | clear |
| film on glass + water drop after drying | clear | clear | clear | clear | clear |
| viscosity - Brookfield ULA 25° C. @ 12 rpm | 17.4 | 16.9 | 22.2 | 24.7 | 19.1 |
| High Humidity Curl Retention Evaluation, % hair spray retained (average value/ standard deviation) | | | | | |
| 1.5 hour | 96.9/2.5 | 97.3/0.3 | 97.0/1.1 | 96.5/3.3 | 95.7/2.6 |
| 4 hour | 95.6/2.6 | 96.4/2.1 | 96.1/1.0 | 93.4/4.1 | 92.2/4.5 |
| 24 hour | 95.6/2.6 | 96.0/1.9 | 95.7/1.4 | 93.4/4.1 | 91.4/4.3 |

Example 40: Hair Gel Formulations

Two hair gel formulas were prepared using the polymer of Example 8 after drying the solution to yield a powder. The gels exhibited only a slight haze, and had viscosities of 9,500 cP and 7,500 cP, respectively.

TABLE 3

Hair gel formulas of Example 40

| ingredient | formula (w/w) | |
|---|---|---|
| | A | B |
| water | 96.85 | 97.25 |
| tetra sodium EDTA (Versene ® 100) | | 0.10 |
| carbomer (Ashland ™ 940) | 0.50 | 0.50 |
| aminomethyl propanol (95%) | 0.65 | 0.65 |
| polymer of Example 8 | 1.00 | 1.00 |
| phenoxy ethanol and caprylyl glycol (Optiphen ™) | 1.00 | |
| propylene glycol (and) diazolidinyl urea (and) iodopropynyl butylcarbamate (Liquid Germall ™ Plus) | | 0.50 |
| total: | 100.00 | 100.00 |
| appearance | slight haze | slight haze |
| Brookfield viscosity, 25 C., Spindle: TC, 10 rpm | 9500 | 7500 |

Example 41: SPF 30 Sun Care Composition

An anhydrous, water-resistant sun care composition is made having the ingredients and addition levels shown in Table 4. This formula has a theoretical sun protection factor (SPF) of 30.

TABLE 4

The anhydrous sunscreen of Example 41

| ingredient | trade name | addition level (wt %) |
|---|---|---|
| sub-formulation I | | |
| ethanol | | 38.0 |
| polymer of Example 8 | | 2.0 |

TABLE 4-continued

The anhydrous sunscreen of Example 41

| ingredient | trade name | addition level (wt %) |
|---|---|---|
| sub-formulation II | | |
| avobenzone | Escalol ™ 517 | 2.0 |
| oxybenzone | Escalol ™ 567 | 4.0 |
| homosalate | Eusolex ™ HMS | 15.0 |
| octisalate | Escalol ™ 587 | 5.0 |
| sub-formulation III | | |
| diisopropyl adipate | Ceraphyl ™ 230 | 12.0 |
| isodecyl neopentanoate | Ceraphyl ™ SLK | 14.0 |
| isostearyl neopentanoate | Ceraphyl ™ 375 | 8.0 |
| total | | 100.0 |

Example 42: SPF 70 Sun Care Composition

An anhydrous, water-resistant sun care composition is made having the ingredients and addition levels shown in Table 5. This formula has a theoretical sun protection factor (SPF) of 70.

TABLE 5

The anhydrous sunscreen of Example 42

| ingredient | trade name | addition level (wt %) |
|---|---|---|
| sub-formulation I | | |
| ethanol | | 37.0 |
| polymer of Example 8 | | 2.0 |
| sub-formulation II | | |
| avobenzone | Escalol ® 517 | 3.0 |
| oxybenzone | Escalol ® 567 | 6.0 |
| homosalate | Eusolex ® HMS | 15.0 |
| octisalate | Escalol ® 587 | 5.0 |
| octocrylene | Escalol ® 597 | 10.0 |
| sub-formulation III | | |
| diisopropyl adipate | Ceraphyl ® 230 | 10.0 |
| isodecyl neopentanoate | Ceraphyl ® SLK | 12.0 |
| total | | 100.0 |

What we claim is:
1. A non-homopolymer polymer synthesized from monomers consisting of:
   (A) 24-26 mole percent of at least one monomer selected from the group consisting of: N-vinyl-2-pyrrolidone, N-vinyl-2-caprolactam, and combinations thereof,
   (B) 24-26 mole percent of a (meth)acrylic acid, and combinations thereof,
   (C) 35-38 mole percent of at least one monomer selected from the group consisting of: methyl (meth)acrylate, iso-butyl (meth)acrylate, trifluoroethyl (meth)acrylate, t-butylaminoethyl (meth)acrylate, and combinations thereof,
   (D) 12-13 mole percent di-iso-butyl fumarate, and
   (E) up to 5 mole percent of a monomer selected from the group consisting of: PEG/PPG (meth)acrylate, and combinations thereof,
   wherein:
   the total monomer content adds to 100 mole percent,
   the non homopolymer has a glass transition temperature of at least 80° C., and the non-homopolymer is soluble up to 50% (w/w) in a lower molecular weight alcohol.

2. A formulation comprising a non-homopolymer is-synthesized from monomers consisting of:
- (A) 24-26 mole percent of at least one monomer selected from the group consisting of: N-vinyl-2-pyrrolidone, N-vinyl-2-caprolactam, and combinations thereof,
- (B) 24-26 mole percent of a (meth)acrylic acid, and combinations thereof,
- (C) 35-38 mole percent of at least one monomer selected from the group consisting of: methyl (meth)acrylate, iso-butyl (meth)acrylate, t-butylaminoethyl (meth)acrylate, trifluoroethyl (meth)acrylate, and combinations thereof,
- (D) 12-13 mole percent di-iso-butyl fumarate, and
- (E) up to 5 mole percent of a monomer selected from the group consisting of: a PEG/PPG (meth)acrylate, and combinations thereof, wherein:
the total monomer content adds to 100 mole percent,
the non-homopolymer has a glass transition temperature of at least 80° C., and
the non-homopolymer is soluble up to 50% (w/w) in a lower molecular weight alcohol.

* * * * *